(12) United States Patent
Lee et al.

(10) Patent No.: US 7,700,109 B2
(45) Date of Patent: *Apr. 20, 2010

(54) BIOMOLECULE TRANSDUCTION MOTIF MPH-1-BTM AND THE USE THEREOF

(75) Inventors: Sang-Kyou Lee, Seoul (KR); Seung-Kyou Lee, Kyeunggi-Do (KR)

(73) Assignee: ForHumanTech. Co., Ltd., Suwon (KR)

(*) Notice: Subject to any disclaimer, the term of this patent is extended or adjusted under 35 U.S.C. 154(b) by 229 days.

This patent is subject to a terminal disclaimer.

(21) Appl. No.: 11/267,817

(22) Filed: Nov. 7, 2005

(65) Prior Publication Data

US 2006/0148060 A1 Jul. 6, 2006

Related U.S. Application Data

(63) Continuation-in-part of application No. 10/501,665, filed as application No. PCT/KR03/00122 on Jan. 20, 2003, now abandoned.

(30) Foreign Application Priority Data

Jan. 19, 2002 (KR) .................. 10-2002-0003183

(51) Int. Cl.
*A61K 39/00* (2006.01)
*A61K 39/02* (2006.01)
*A61K 39/38* (2006.01)

(52) U.S. Cl. ................ 424/185.1; 424/9.1; 424/9.2; 424/184.1; 424/190.1; 424/192.1; 530/300; 530/350

(58) Field of Classification Search ............ 424/9.1, 424/9.2, 184.1, 185.1, 190.1, 192.1; 530/300, 530/350

See application file for complete search history.

(56) References Cited

U.S. PATENT DOCUMENTS

| 6,166,191 A * | 12/2000 | Randazzo ............... 536/23.5 |
|---|---|---|
| 2003/0104622 A1 | 6/2003 | Robbins et al. |
| 2003/0229202 A1 | 12/2003 | Guo et al. |
| 2005/0090646 A1 | 4/2005 | Sullivan |
| 2005/0158373 A1 | 7/2005 | Szeto et al. |
| 2008/0132450 A1 | 6/2008 | Lee et al. |

FOREIGN PATENT DOCUMENTS

| WO | WO98/07858 | * | 2/1998 |
|---|---|---|---|
| WO | WO98/07860 | * | 2/1998 |
| WO | WO 03/059940 A1 | | 7/2003 |
| WO | WO 2004/044008 A1 | | 5/2004 |
| WO | WO 2004/078933 A2 | | 9/2004 |

OTHER PUBLICATIONS

Alkema, M.J., et al., "Identification of Bmi 1-interacting proteins as constituents of a multimeric mammalian Polycomb complex," *Genes & Dev.* 11:226-240, Cold Spring Harbor Laboratory Press (1997).

Gunster, M.J., et al., "Identification and Characterization of Interactions between the Vertebrate Polycomb-Group Protein BMI1 and Human Homologs of Polyhomeotic," *Mol. Cell. Biol* 17:2326-2335, American Society for Microbiology (1997).

Ohta, H., et al., "Structure and Chromosomal Localization of the R4E28/HPH1 Gene, a Human Homologue of the *Polyhomeotic* Gene," *DNA Seq.* 11:61-73, (OPA) Overseas Publishers Association N. V. (2000).

Kühnel, F., et al., "Protein Transduction Domains Fused to Virus Receptors Improve Cellular Virus Uptake and Enhance Oncolysis by Tumor-Specific Replicating Vectors," *J. Virol.* 78:13743-13754, American Society for Microbiology (Dec. 2004).

Lee, K.-M., et al., "Molecular Basis of T Cell Inactivation by CTLA-4," *Science* 282:2263-2266, American Association for the Advancement of Science (1998).

International Search Report for International Application No. PCT/IB2006/003971, Korean Intellectual Property Office, Republic of Korea, mailed on Sep. 19, 2007.

Asemu, G., et al., "Identification of the changes in phospholipase C isozymes in ischemic-reperfused rat heart," *Arch. Biochem. Biophys.* 411:174-182, Elsevier Science (Mar. 2003).

Choi, H.S., et at. , "Transduced Tat-α-Synuclein Protects against Oxidative Stress In vitro and In vivo," *J. Biochem. Mol. Biol.* 39:253-262, Korean Society for Biochemistry and Molecular Biology (May 2006).

Dent, M.R, et al., "Phosphohpase C gene expression, protein content, and activities in cardiac hypertrophy and heart failure due to volume overload," *Am. J. Physiol. Heart Circ. Physiol.* 287:H71 9-H727, The American Physiological Society (Apr. 2004).

Dietz, G.P.H. et al., "Inhibition of Neuronal Apoptosis in VItro and in Vivo Using TAT-Mediated Protein Transduction," *Mol. Cell. Neurosci.* 21:29-37, Elsevier Science (Sep. 2002).

Krief, S., et al., "Identification and Characterization of cvHSP," *J. Biol. Chem.* 274:36592-36600, The American Society for Biochemistry and Molecular Biology, Inc. (1999).

Lai, Y., et al., "Selectively increasing inducible heat shock protein 70 via TAT-protein transduction protects neurons from nitrosative stress and excitotoxicity," *J. Neurochem.* 94:366, International Society for Neurochemistry (Jul. 2005).

Mangat, R., el al., "Inhibition of phospholipase C-$\gamma_1$ augments the decrease in cardiomyocyte viability by $H_2O_2$," *Am. J. Physiol. Heart Circ. Physiol.* 291:H854-H860, The American Physiological Society (Feb. 2006).

(Continued)

*Primary Examiner*—Rodney P. Swartz
(74) *Attorney, Agent, or Firm*—Sterne, Kessler, Goldstein & Fox P.L.L.C.

(57) ABSTRACT

This invention relates to a novel Biomolecule Transduction Motif (BTM), Mph-1 peptide (Mph-1-BTM), which has the potential to transduce many biological response modifiers effectively into the cytoplasm, intracellular organelles or nucleus of prokaryotic or eukaryotic cells in vivo and in vitro, and the related technological methods using Mph-1-BTM. This Mph-1-BTM can be used in the development of new recombinant protein vaccines or DNA/RNA vaccines, gene and protein therapy, production of pharmacologically or medicinally useful proteins, or pharmaco-medicinal drug therapy.

22 Claims, 20 Drawing Sheets

OTHER PUBLICATIONS

Noguchi, H., et al., "A new cell-permeable peptide allows successful allogenic islet transplantation in mice," *Nat. Med.* 10:305-309, Nature Publishing Company (Feb. 2004).

Wheeler, D.S., et al., "Intracellular delivery of HSP70 using HIV-1 Tat protein transduction domain," *Biochem Biophys. Res. Commun.* 301:54-59, Elsevier Science (Jan. 2003).

Yagisawa, H., "Nucleocytoplasmic Shuttling of Phospholipase C-$\delta_1$: A Link to $Ca^{2+}$," *J. Cell. Biochem.* 97:233-243, Wiley-Liss, Inc. (Oct. 2005).

International Search Report for International Application No. PCT/IB2007/003404, Korean Patent Office, Republic of Korea, mailed on May 2, 2008.

International Search Report for International Application No. PCT/IB2007/004189, Korean Patent Office, Republic of Korea, mailed on Jun. 9, 2008.

Co-pending U.S. Appl. No. 11/878,431, inventors Lee, S-K., et al., filed Jul. 24, 2007 (Not Yet Published).

\* cited by examiner

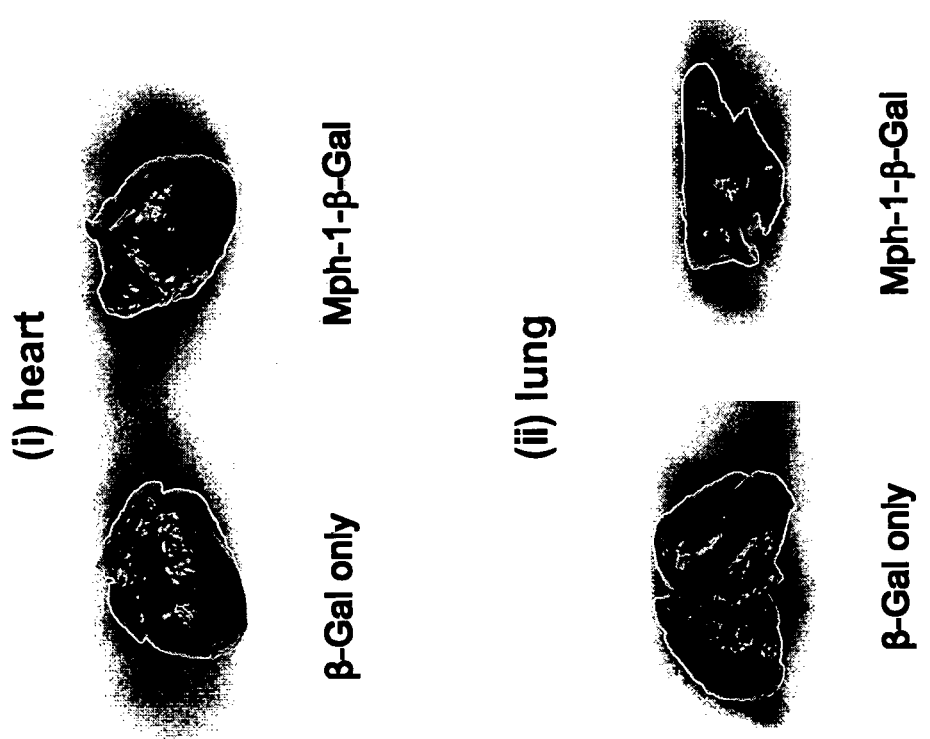

FIG. 8A
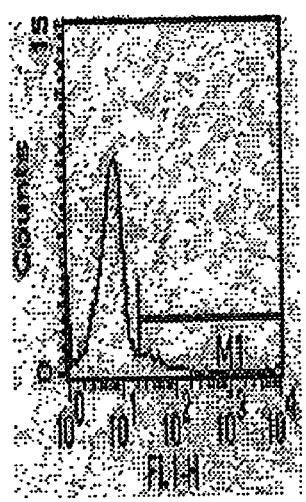 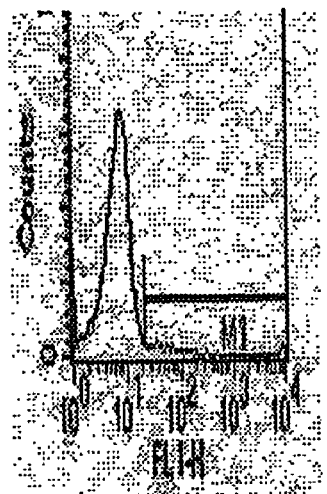 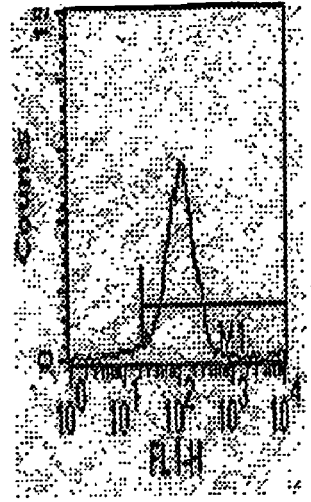
Mph-1  pCD8-ζ-5XGBS  Mph-1
+ pCD8-ζ-5XGBS FIG. 8B
Isotype control
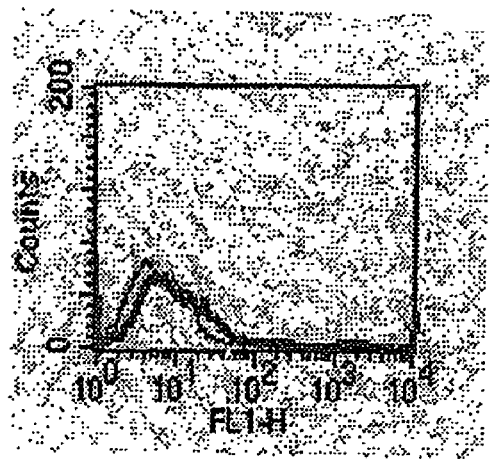
Spleenocyte
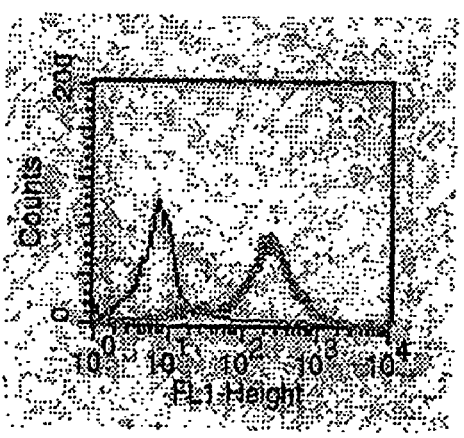
T cell
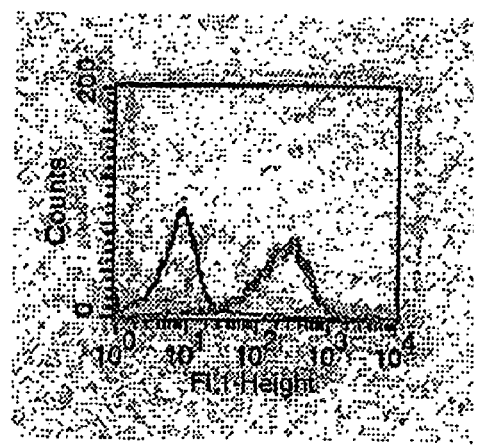

FIG. 9
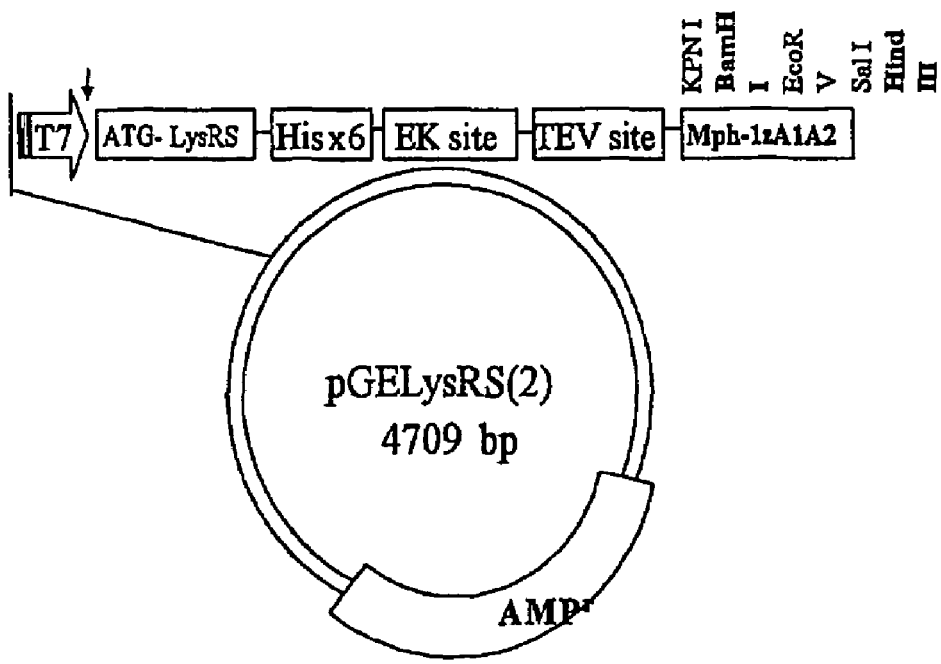
(a)
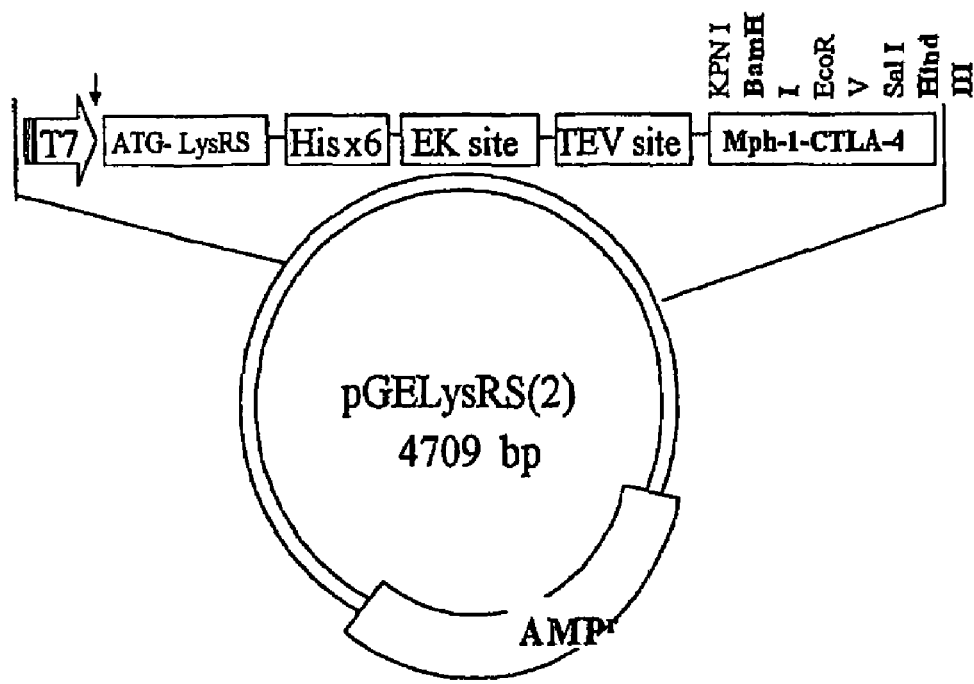
(b)

FIG.10
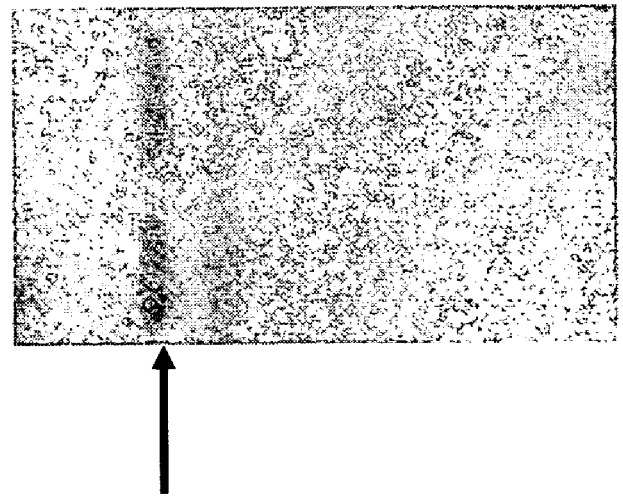
(B)
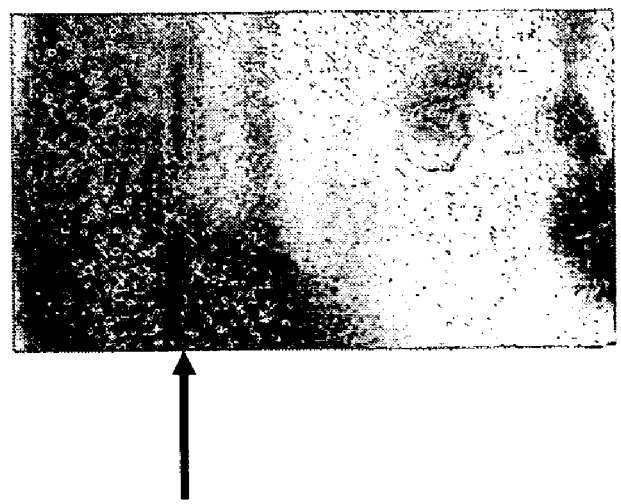
(A)

FIG.11   15 min later   30 min later

BIOMOLECULE TRANSDUCTION MOTIF MPH-1-BTM AND THE USE THEREOF

CROSS REFERENCE TO RELATED APPLICATIONS

This application is a Continuation-in-Part (CIP) of U.S. patent application Ser. No. 10/501,665 filed on Feb. 11, 2005, now abandoned, which is the National Stage of International Application No. PCT/KR03/00122, filed on Jan. 20, 2003, which claims priority from Korean Patent Application No. 10-2002-0003183, filed on Jan. 19, 2002.

BACKGROUND OF THE INVENTION

1. Field of the Invention

This invention relates to Mph-1 Biomolecule Transduction Motif (Mph-1-BTM), a novel intracellular biomolecule transduction peptide, which delivers biologically active, functional or/and regulatory molecules in vivo and in vitro into the cytosol, organelles or nucleus of prokaryotic and eukaryotic cells, and the utilization of the same.

2. Background Art

Generally, living cells are not permeable to macromolecules such as proteins or nucleic acids. The fact that only small-size molecules can permeate through the membrane of living cells at very low rates has restricted the research to develop drugs to cure, prevent or diagnose diseases using macromolecules including, for example, proteins and nucleic acids. On the other hand, because most of the substances manufactured to cure, prevent or diagnose certain diseases have to be delivered into the cytosol with their effective amounts, there have been several methods developed delivering those substances from the cell surface of the target cell into the cell.

Methods used to deliver macromolecules into cells include electroporation, cytosol fusion using liposomes, a highly concentrated projection technique of a projectile coated with DNA on the surface, calcium-phosphorous-DNA precipitation method, DEAE-dextran transfection, infection with modified viral nucleic acids, and direct microinjection into a single cell, etc. Moreover, there have been attempts to deliver macromolecules using nanoparticles in vitro and in vivo these days, but it is only in its beginning step technologically and clinically. Furthermore, these methods can deliver macromolecules to only a few of the target cells, and its efficiency is not sufficient enough to be applied clinically. Also, most of these methods cause side effects on the other cells.

In this regard, the demand of the development of a novel method of delivering biologically active macromolecules into the target cells effectively in vivo and in vitro is increasing (L. A. Sternson, *Ann. N.Y. Acad. Sci.* 57:19-21(1987)). Chemical addition of lipid peptide (P. Hoffmann et al., *Immunobiol.* 177:158-170(1988)) or use of base polymers such as polylysine or polyarginine (W-C. Chen et al., *Proc. Natl. Acad Sci., USA.* 75:1872-1876(1978)) were provided. In addition, it was reported that folate of a transporter was transferred into a cell in the form of a folate-conjugate. But it has not been confirmed yet that the folate was transduced into the cytosol. Also, *Pseudomonas* Exotoxin is known as a transporter (T. I. Prior et al., *Cell* 64:1017-1023(1991)). However, the effects of biologically active macromolecules delivered into the cytosol and their general application have not been clearly verified yet. Therefore, an effective method of transducing biologically active macromolecules into cytosol and nucleus of living cells is highly demanded.

In addition, the efficient delivery of DNA/RNA as well as macromolecules, such as proteins, into cells in vivo and in vitro is considered to be one of the essential techniques required in the field of biotechnology and applied medical science. The delivery of DNA/RNA into cells acts as a decisive factor for gene therapies, for studying the relation of the function of a protein encoded by the gene in vivo and in vitro, and for the development of novel remedies using DNA/RNA. However, since DNA/RNA cannot permeate the cell membrane efficiently, it is very important for using genes in basic and clinical researches to improve the permeability.

For this reason, liposomes, nanomolecules, and viral vectors etc. are developed to deliver DNA and/or RNA into a cell in vitro and in vivo, and the possibilities of the use thereof were examined and investigated. However, concerning beneficial-effects and side effects, it has numerous problems to be resolved. In particular, regarding liposomes, since the side effects against cells and the cytotoxicity are very serious, their application was limited to basic research. As for nanomolecules, though it has been receiving attention these days, the decomposition of carrier particles in vivo, the poor efficiency of transduction and the immunological responses elicited by the molecules should be studied further and should be resolved. As for retroviruses, it has a problem in that it cannot infect undividing cells. Adenovirus or adeno-associated virus vector also has a very limited clinical application. Furthermore, these two types of viral vectors may elicit immune responses against the other viral proteins, so its treating efficiency has many doubts. Therefore, a new way to transduce DNA/RNA into cells efficiently and less detrimentally is needed.

Meanwhile, proteins regulating physiological phenomena in vivo, are produced by bacteria, such as *E. coli*, as a form of recombinant protein, and have been employed in the treatment of numerous diseases. The proteins, which were synthesized in bacteria, however, were known to be inefficient in folding structures and functions in comparison to the naturally folded proteins in vivo. Thus, there have been lots of attempts to produce proteins in yeasts, insect cells or animal cells, and to make the proteins produced in bacteria refolded using transgenic animals. However, these methods require further studies and full understanding on many molecular cell biological intermediate steps, and their transduction efficiencies are very low. And they are not cost effective.

Several PTDs (Protein Transduction Domain) have been reported as a result of this demand. Among them, Tat protein, which is a Human Immunodeficiency Virus-1 (HIV-1) viral protein, has been mostly well studied. The Tat protein was known to operate more efficiently when containing amino acids 47 to 57 (YGRKKRRQRRR) (SEQ ID NO:19), where positive charged amino acids are concentrated, than continuing full-length 86 amino acid protein (Fawell S. et al., *Proc. Natl. Acad. Sci. USA* 91:664-668(1994)). Other examples of PTDs are amino acids 267 to 300 of Herpes Simplex Virus type 1 protein (HSV-1) (Elliott G. et al., *Cell* 88:223-233 (1997)), amino acids 339 to 355 of Antennapedia (ANTP) protein of *Drosophila* (Schwarze S. R. et al., *Trends Pharmacol Sci.* 21:45-48(2000)), and artificial combinations of positively charged amino acids. Regarding the PTDs mentioned above, we, inventors, found that they contained lysine and arginine abundantly, wherein the arginine was considered to play a great role in the transduction of biomolecule into cells. And it was supported by the published document that disclosed transduction activities of artificial peptides consisting of positively charged amino acids. (Laus R. et al., *Nature Biotechnol.* 18:1269-1272(2000)).

With regard to the transduction mechanism of macromolecules into cells when using PTDs, there are 2 (two) hypotheses. The first is that PTDs ruin the plasma membrane, and transmit the molecules across it. The second one is that PTD uses the plasma membrane to form a new vesicle that can carry the molecules into the cells. Moreover, there are suppositions that PTD has structural features that can form new channels in the membrane (Becker-Hapak M. et al., *Methods* 24(3):247-256 (2001)).

However, experiments with artificially combined amino acids with 12 arginines and 12 lysines suggested that the hypothesis that the existence of lysine and arginine at specific positions induced the formation of new channels might be wrong (Rothbard J. B., et al., *Nature Med.* 6(11):1253-1257 (2000)). In addition, considering the facts that only the proteins, which were bound covalently or non-covalently to PTDs, were transferred through the cell membrane, the hypothesis, that PTDs ruin the plasma membrane and translocate the molecules across it, was not acceptable. Furthermore, according to our studies, PTDs represented transduction abilities both at 37° C. and at 4° C., which suggested that PTD neither made new channels nor made new vesicles.

Recently, as a new type of PTD, Membrane Translocating Sequence (MTS) was developed. Its amino acid sequence was synthesized based on the signal peptide of FGF (Fibroblast Growth Factor), while amino acids of the signal peptide were known to have features quite different from those of PTD amino acids as follows: (a) 3-5 numbers of arginines or lysines exist non-continuously together with serine or threonine, and there are no glutamic acid and aspartic acid, (b) one or more basic amino acids, and 6-12 numbers of hydrophobic amino acids, (c) serine, threonine, or small size hydrophobic amino acid exists abundantly, and glutamine, aspartic acid are present in small amount, (d) 10 random amino acids are present between 1 or 2 basic amino acid(s) that are gathered together. Thus, the MTS is thought to have different features in comparison to the ordinary PTDs. That is, the MTS has a different amino acid combination.

In this regard, we have tried to find out a new machinery as to the PTD transduction and decisive factors to the amino acid combination consisting of PTDs, based on the discovered features of the two types of PTDs above mentioned and based on the results of our preliminary researches. The following are two new hypotheses derived from the decisive factors and requisites for the development of a new type of PTD of the present invention: 1) considering that i) unfolded proteins are transduced more efficiently than completely folded ones, and that ii) once the unfolded proteins are transmitted into organelles or cells they are not eliminated from the organelles or cells, and that iii) PTDs do not utilize receptors to perform endocytosis or phagocytosis, it seems that the PTDs use channels present on the cell surface. Accordingly, hydrophobic amino acids, such as alanine and valine, are highly demanded; 2) Since PTDs transmit molecules into the nucleus efficiently, its function may be similar to transcription factors. Therefore, PTDs would be found frequently in transcription factors. And the PTDs may use channels similar to translocons that transmit proteins into organelles.

Based on these two hypotheses and requisites, we searched the gene bank. With the factor that the conventional PTDs have lysines and arginines abundantly, we selected about 10,000 primary candidate genes. Among them, 500 genes were chosen by applying the requisites of signal peptide, and 100 genes of the 500 genes were confirmed as to have alanine and valine. Finally, 20 genes were selected by applying the factors required for the transcription factors, and then the transduction efficiencies were tested therefor. In addition, fusion proteins of each of these candidate PTDs and β-galactosidase were expressed and purified, and the functions of these proteins were detected using Jurkat T cells. As a consequence, amino acid sequence 858 to 868 of Mph-1 (number of gene bank: U63386), a mouse transcription factor, was found to have unexpectedly significant transduction ability and was named Mph-1-BTM (Biomolecule Transduction Motif).

Thus, we completed the present invention with the findings that amino acids 858 to 868 of Mph-1 have significantly excellent features as an intracellular biomolecule transduction peptide, thereby any target proteins, nucleic acids, lipids, carbohydrates and chemical compounds can be efficiently delivered into cytosol and nucleus in vivo and in vitro. Furthermore, we found that an expression vector having 5 (five) successive DNA/RNA sequences, which specifically bind to DNA/RNA binding domains, could be transduced in vivo and in vitro into the specific organs or cells, using the Mph-1-BTM and using the DNA/RNA binding domains (DBD and/or RBD) that bind to the DNA/RNA to be transduced, wherein the expression vector could include regulatory elements comprising a promoter that induces gene expression selectively in specific organs, tissues or cells.

BRIEF DESCRIPTION OF THE DRAWINGS/FIGURES

FIG. 8A represents the transduction of expression vector of pCD8-ζ-5XGBS into T cells using Mph-1-BTM.

FIG. 8B represents the transduction of expression vector of pCD8-ζ-5×GBS into T cells and splenocyte in blood in vivo and the expression thereof.

FIG. 9 illustrates the construct of expression vector of pMph-1-zA1A2(a) and pMph-1-CTLA4(b).

FIG. 10 shows coomassie blue staining of purified fusion proteins of pMph-1-zA1A2(a) and pMph-1-CTLA4(b).

FIG. 11 shows the transmission of β-gal proteins into callus cells using Mph-1-BTM.

Figure 1A:
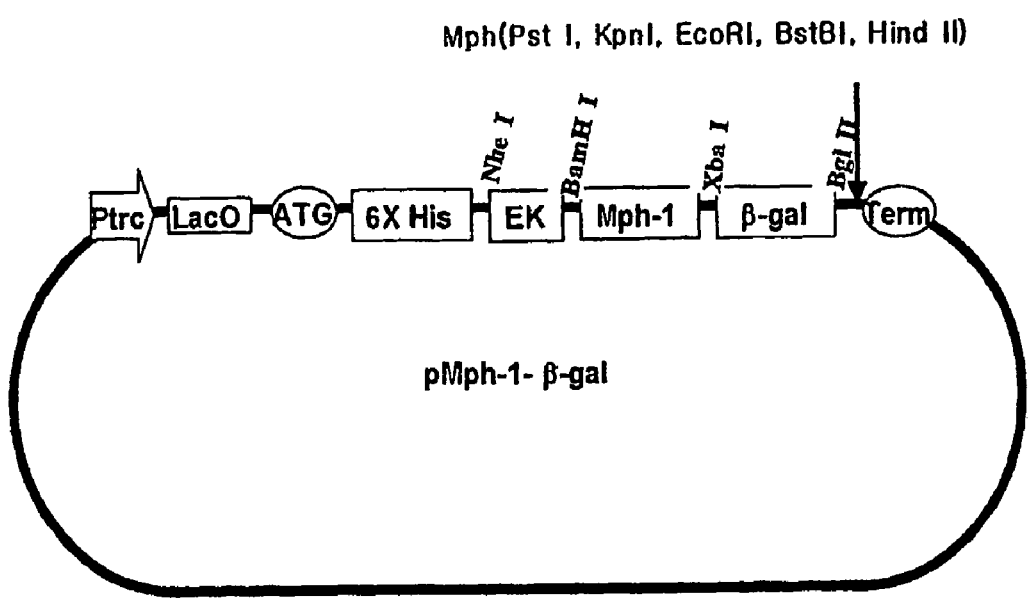
FIG. 1A illustrates the construct of expression vector pMph-1-β-gal.

Below are more detailed descriptions according to practical examples. Below practical examples are there to show examples, and this invention is not limited to this range. Moreover, the technical reference of this invention is combined to the invention as a reference.

DETAILED DESCRIPTION OF THE INVENTION

The object of this invention is to provide a novel biomolecule transduction motif Mph-1-BTM (SEQ ID NO:1), which effectively transduces biologically active, functional regulatory macromolecules in vivo and in vitro via numerous administration routes including intramuscular, intraperitoneal, intravein, oral, nasal, subcutaneous, intradermal, mucosal, and inhalation routes and to provide the recombinant expression vector including it.

Another object of this invention is to provide a recombinant expression vector comprising Mph-1-BTM and to provide transformed cells using the vector.

Another object of this invention is to provide the fusion protein of biomolecule transduction motif and a desired protein by transforming a suitable host cell with the recombinant expression vector.

Another object of this invention is to provide a method of transducing biologically active functional modulatory macromolecules in vivo and in vitro into the cytosol or nucleus of prokaryotes or eukaryotes using Mph-1-BTM.

Another object of this invention is to use the Mph-1-BTM in gene therapies and in disease treatment using proteins.

Another object of this invention is to provide a recombinant vaccine including Mph-1-BTM and a DNA/RNA vaccine, or delivering genes for gene therapies using Mph-1-BTM.

Another object of this invention is to provide a novel vaccine using DNA/RNA or protein antigens specific to pathogens, such as viruses, bacteria, mold, and various cancer cells.

Another object of this invention is to provide a genetic medicine of DNA/RNA, which regulates biological activities in vivo and in vitro, using Mph-1-BTM.

In order to achieve these objects, this invention provides a peptide or its active fragment comprising amino acid sequence (SEQ ID NO:1) to transduce biologically active functional modulatory macromolecules in vivo and in vitro into the cytosol or nucleus of prokaryotes or eukaryotes.

Furthermore, this invention provides a peptide or its active fragment comprising amino acid sequence (SEQ ID NO:1) to transduce biologically active functional modulatory macromolecules in vivo and in vitro into the cytosol or nucleus of prokaryotes or eukaryotes, wherein a part of the amino acid sequence is deleted or substituted, or at least a part of the amino acid sequence is replaced by L- or D-form amino acids, or the structure of amino acid is reformed to enhance stability in vivo.

Furthermore, this invention provides DNA encoding intracellular biomolecule transduction peptide, recombinant DNA expression vector comprising DNAs encoding target protein, and transformed *E. coli* of DH5a Mph-1(KCCM 10345) using the vector.

Furthermore, this invention provides a method of transducing a complex of the peptide (or the peptide fused with a target protein) and biologically active functional regulatory molecule (for example, chemical drug or chemical prodrug) via numerous administration routes including intramuscular, intraperitoneal, intravenous, oral, nasal, subcutaneous, intradermal, mucosal and inhalation routes, in vivo and in vitro into the cytosol or nucleus of prokaryotes or eukaryotes. The following describes this invention in detail.

In this specification and claims, "biologically active functional modulatory molecule" means the molecule, which regulates any physiological phenomenon, including, for example, DNA, RNA, protein, lipids, carbohydrates, and chemical compounds.

In addition, "an active fragment" is defined as some part of the amino acid sequence of SEQ ID NO:1 or its modified one in which a part of the amino acid is deleted or substituted, or at least a part of the amino acid sequence is replaced by L- or D-form amino acids, or the structure of amino acids is reformed to enhance stability in vivo, wherein the fragment maintains intracellular biomolecule transduction activities.

In addition, "macromolecule" is defined as to include proteins, lipids, nucleic acids, carbohydrates and chemical compounds.

In addition, a biomolecule transduction peptide of "Mph-1-BTM derivative" is defined as a peptide or its active fragment, which maintains transduction activities of Mph-1-BTM, wherein a part of the amino acid sequence is deleted or substituted, or at least a part of the amino acid sequence is replaced by L- or D-form amino acids, or the structure of amino acids is reformed to enhance stability in vivo and in vitro.

In addition, a "fusion protein" is defined as a protein fused with a biomolecule transduction peptide of Mph-1-BTM directly through chemical, physical, covalent or non-covalent bond, or indirectly through any mediator.

In addition, a "chemical compound" is defined as a chemical substance, which regulates a cell's function, such as anticancer drug, immunological disease drug, antiviral drug and growth, development or differentiation factor of an animal.

In this invention, a biomolecule transduction peptide is defined as a peptide corresponding to amino acids from $858^{th}$ to $868^{th}$ from N-terminus of mouse transcription inhibitor Mph-1 (M. J. Alkema et al., *Genes Dev.* 12:226-240 (1997)), wherein arginines and alanines are considered as to interact with biomolecule transducing channel receptors on the cell surface.

In addition, this invention relates to a peptide corresponding to the amino acid sequence of SEQ ID NO:1, wherein a portion of the amino acid sequence including arginine, valine and alanine is substituted with functionally and structurally similar amino acids, for example, valine, etc.

This invention also provides an expression vector comprising: i) DNA/RNA encoding a biomolecule transduction peptide corresponding to amino acid sequence of SEQ ID NO:1, or DNA/RNA encoding a biomolecule transduction peptide corresponding to modified amino acid sequence of SEQ ID NO:1 in which a part of the amino acid sequence is deleted or substituted or at least a part of the amino acid sequence is replaced by L- or D-form amino acids, or DNA/RNA encoding an active fragment of the peptide; and DNA/RNA encoding a desired protein and/or biologically active functional regulatory molecules to be introduced into cells. This recombinant expression vector preferably includes tag sequence(s), such as a series of Histidine, Hemaglutinin, Myc, or Maltose binding protein codon, and so forth, in order to make the purification easier. Furthermore, in order to increase solubility, a fusion partner, such as lysine RNA polymerase, can be introduced to the vector. Furthermore, for the flexibility of the protein encoded by the genes and for the stability of the fusion protein, one or more glycine and spacer amino acids including AYY amino acids can be incorporated. Furthermore, a cleavage site recognized by a protease specifically present in a certain intracellular organelle to remove unwanted part of the fusion protein or to separate BTM and the cargo molecule, expression regulatory sequence and a marker to monitor the transduction or a reporter gene can be inserted into the expression vector, wherein the expression regulatory sequence consists of regulatory domain comprising a promoter or enhancer that is specific to cells, tissues or organs to which the desired DNA/RNA is transduced.

In one embodiment, recombinant expression vector including intracellular biomolecule transduction peptide of pMph1-β-gal comprises DNAs encoding a peptide corresponding to amino acid sequence of SEQ ID NO:1, 6 (six) successive histidine codons to purify the desired proteins expressed in host cells, Asp-Asp-Asp-Asp-Lys (SEQ ID NO:20) sequence to be cleaved with enterokinase or Glu-Asn-Leu-Tyr-Phe-Gln-Gly (SEQ ID NO:21) sequence to be cleaved with Tev and DNAs encoding a marker of β-galactosidase for the detection of the desired protein in cells.

The pMph-1-β-gal vector of this invention can easily be obtained with ordinary PCR (polymerase chain reaction) methods using pIND/lacZ vector (can be obtained from Invitrogen Inc.) as a template. Also, in this invention, biomolecule transducing recombinant expression vector is manufactured by cutting out β-galactosidase gene with suitable restriction enzyme and replacing it with the desired protein coding DNAs. The desired protein comprises biologically active functional regulatory protein or its fused one, which is chemically or physically bound to ecto domain of ligand that binds specifically to a receptor of cell, tissue or organ to which the desired protein is introduced, in order to transduce it to specific cell or tissue or organ. This ligand or receptor includes protein, lipid, carbohydrate, chemical compound or its complex, but is not limited thereto. If the desired protein is any one of viral specific protein selected from a group consisting of HIV, HBV, HCV and influenza, or a tumor specific protein expressed in tumor cells including liver cancer or stomach cancer cells, the recombinant expression vector of this invention induces CTL (cytotoxic leukocyte) by converting antigen processing pathway from MHC class II to MHC class I. In this case, the recombinant expression vector preferably comprises DNAs encoding one or more ubiquitins.

In one embodiment of the present invention, the desired protein is isolated and purified using the recombinant expression vector. Specifically, after transforming a suitable host cell, such as $E.\ coli$, with the recombinant expression vector of this invention, the desired protein is isolated using interaction between polyhistidine and $Ni^{2+}$-NTA (nitrilotriacetic acid). Furthermore, in another embodiment, a method for transducing functional regulatory molecules are transduced more effectively into cytosol, organelle or nucleus by culturing the recombinant expression vector of the present invention together with biologically active functional regulatory molecules.

In another embodiment, a method of transducing biomolecules is provided as follows: i) providing recombinant expression vector comprising DNAs encoding DNA/RNA binding protein that binds selectively to DBS/RBS (DNA/RNA binding sequence) of the desired DNA/RNA; ii) obtaining protein-DNA/RNA complex by combining the desired DNA/RNA sequence, which contains target DNA/RNA sequence that bids to the DNA/RNA binding protein; and iii) mixed culturing the protein-DNA/RNA complex with cell culture medium in order to transduce the desired DNA/RNA into the cells.

In another embodiment, a method of transducing biomolecule is provided, which comprises: i) obtaining a complex by reacting fusion proteins, which are activated by binding inducer, with the desired chemical compound, wherein the fusion protein is a fused one between the biomolecule transduction peptide of Mph-1 BTM or its derivatives and the desired protein; and ii) mixed culturing the obtained complex together with cell culture medium in order to transduce the desired chemical compounds into the cells. The binding inducers introduced above include binding reagents, for example, BMOE (Pierce Cat. No 2323), DSP (Pierce Cat. No 22585), that bind the biomolecule transduction peptide or the fusion protein between the transduction peptide and the desired protein to DNA/RNA, carbohydrate, lipid, protein or chemical compounds through chemical, physical, covalent or no-covalent bond, directly or indirectly.

Thus, this invention also provides a method of transducing a desired DNA/RNA into cells as follows: i) preparing $1^{st}$ recombinant expression vector comprising a desired DNA/RNA to be transduced into cells, at least one continuous DNA/RNA sequence to which DNA/RNA binding protein binds specifically, and operably linked expression regulatory sequence; ii) preparing $2^{nd}$ recombinant expression vector comprising a peptide of SEQ ID NO:1 or its active fragment, DNA/RNA encoding DNA/RNA binding protein that bind selectively to the DNA/RNA sequence in the $1^{st}$ recombinant expression vector of the step i); iii) collecting expressed fusion protein from host cells using the $2^{nd}$ recombinant expression vector; iv) obtaining a complex of the fusion protein and the desired DNA/RNA by binding the fusion protein of iii) and $1^{st}$ recombinant expression vector of i); v) mixing the complex with the cells, to which the desired DNA/RNA is transferred, and mixed culturing the cells. As a biologically active functional regulatory factor, cytokine such as interleukin-4, interleukin-2, interleukin-12 or γ-interferon, chemokines or EGF can be employed in this invention.

The desired protein of this invention is preferably subject to post-translational modification, for example, ubiquitination, phosphorylation, fatty acylation such as palmistoilation, myristoylation or farnesylation, after translation thereof. In particular, a part of Lck protein amino acid sequence (Met-Gly-Cys-Val-Cys-Ser-Ser-Asn-Pro-Glu-Asp-Asp-Trp-Met-Glu-Asn) (SEQ ID NO:22) can be employed during the acylation process.

Furthermore, when transducing a biological active functional regulatory molecule into cytosol, organelle or nucleus of a cell, it is preferable to use lysosomotrophic agent selected from a group consisting of choroquine, monensin, amantadine, and methylamine in order to enhance the structural and functional safety of the molecule. The biological active functional regulatory molecule is transduced into cytosol, organelle or nucleus of a cell via numerous administration routes, such as intramascular, intraperitoneal, intravein, oral, nasal, subcutaneous, intradermal, mucosal, and inhalation routes, together with the Mph-1-BTM.

Since the biomolecule transducing peptide of the present invention is very small, biological intervention to the active molecule is significantly minimized.

EXAMPLES

Example 1

Figure 1B:
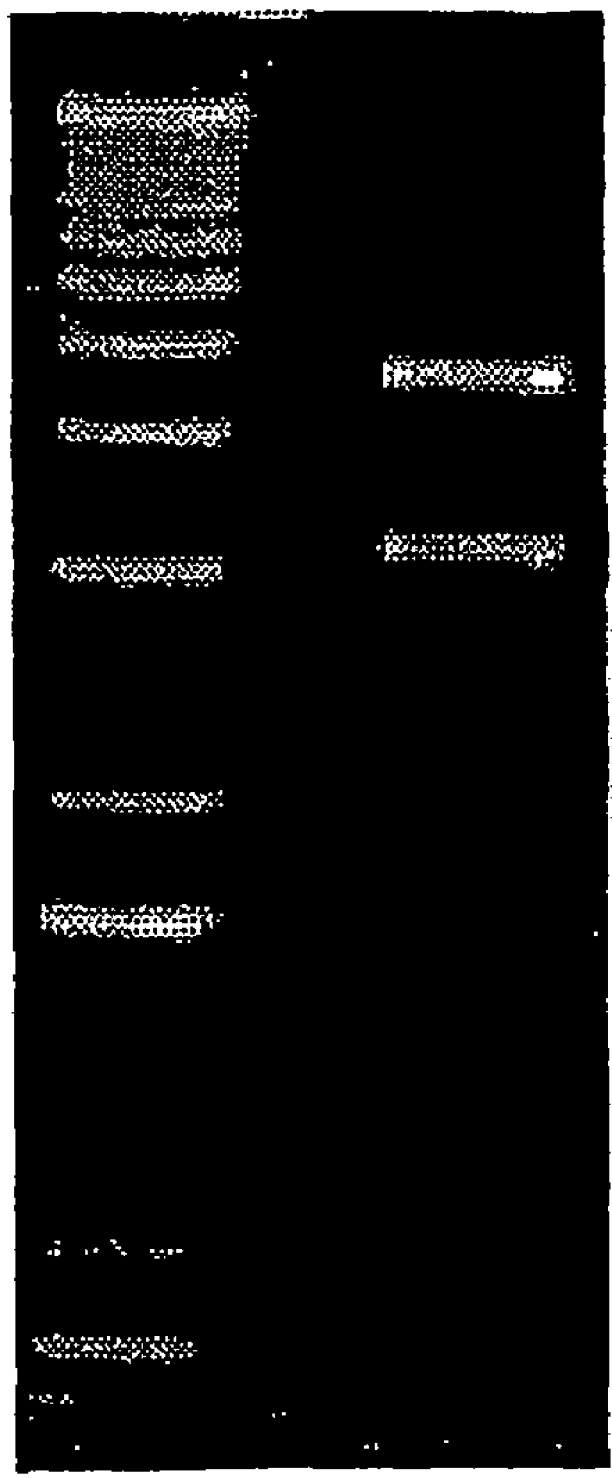
FIG. 1B shows agarose gel images after treating the vector of FIG. 1A with restriction enzymes.

Preparation of Expression Vector Including Mph-1-BTM of Biomolecule Transduction Peptide Nucleic acid sequence encoding peptide corresponding to amino acids from $858^{th}$ of Tyrosine to $868^{th}$ of Arginine from N-terminus mouse transcription factor of Mph-1 (GeneBank Code: U63386) was combined with the nucleic acid sequence encoding reporter protein of β-galactosidase. In order to do this, firstly, a primer of SEQ ID NO:2 containing the nucleic acid sequence encoding peptide corresponding to amino acids from 858$^{th}$ of Tyrosine to 868$^{th}$ of Arginine from N-terminus of Mph-1 and BamHI site for cloning, and a primer of SEQ ID NO:3 containing nucleic acid sequence of 3' terminus of β-galactosidase and restriction enzyme of Bgl II site for cloning were synthesized. Then, PCR was carried out using pIND/lacZ vector (Invitrogen corp.), as a template, with pfu turbo DNA polymerase (Stratagene, cat.# 600252-51). After digesting the PCR products with restriction enzymes of BamHI and Bgl II, the results were purified with PCR purification kit (Quiaquick) (QIAGEN, cat.# 28104). The purified products were cloned to pTrcHis B (Invitrogen, Cat. No. V360-20B), which was purified with gel extraction, at BglII recognition site, thereby recombinant expression vector was generated and named pMph-1-β-gal. FIG. 1A illustrates the construct of the expression vector of pMph-1-O-gal. The expression vector of pMph-1-O-gal was treated with Xba I and Hind III and then, it was subject to electrophoresis on 1% agarose gel followed by staining with ethydium bromide (see FIG. 1B). In FIG. 1B, the second column represents the present pMph-1-β-gal, and the first column represents standard sized DNA fragments.

Example 2

Figure 2:
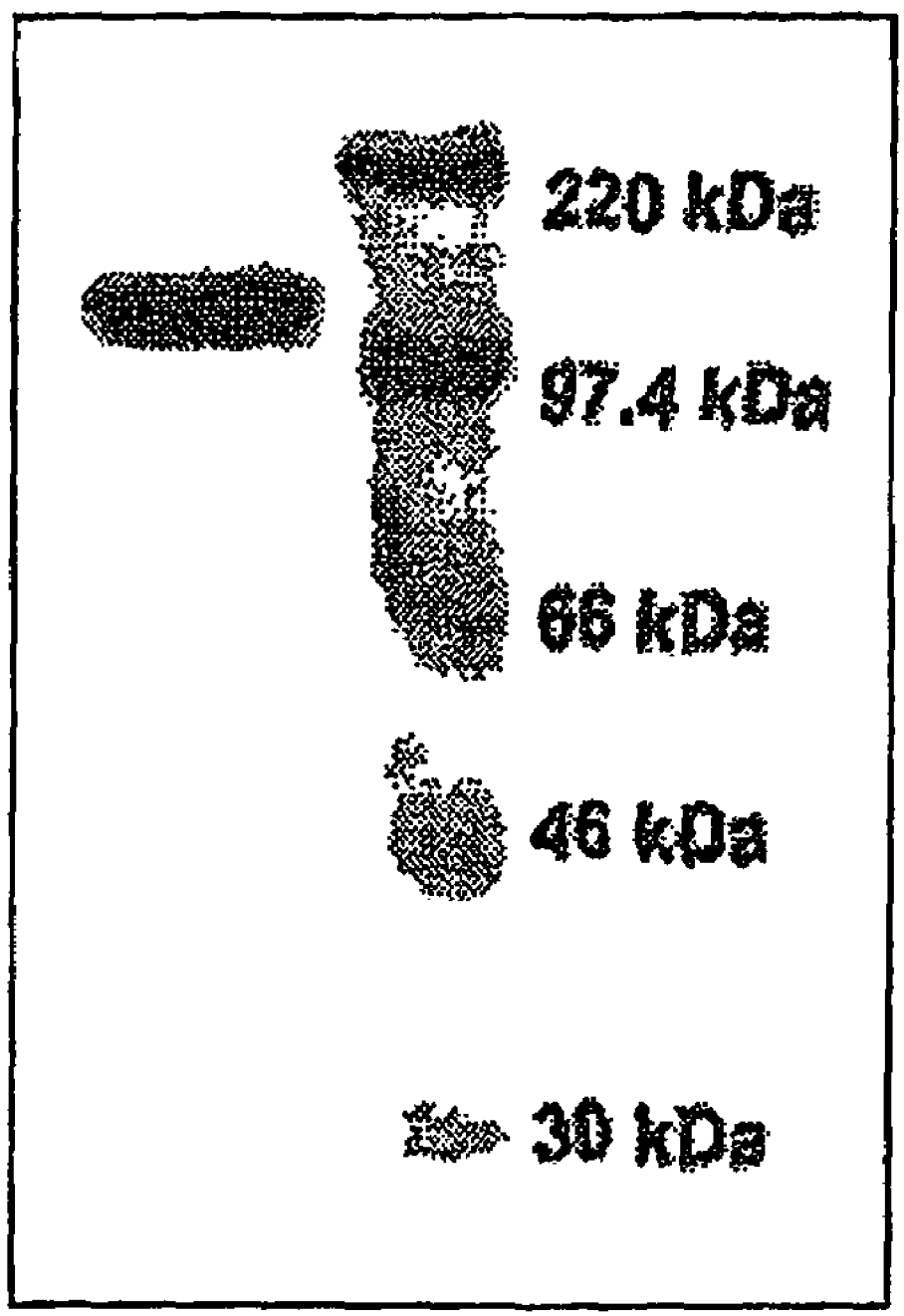
FIG. 2 shows coomasie blue staining of the purified fusion proteins expressed from pMph-1-β-gal vector.

Preparation of *E. Coli* Transformant, and Expression and Isolation of Fusion Protein Therefrom DH5α(ATCC No. 53863) was transformed using pMph-1-β-gal of the Example 1 by heat shock transformation. 2 ml of the transformants were transferred to 100 ml of LB medium, and pre-incubated for 12 hrs at 37° C. with agitation. Then, the pre-incubated transformants were inoculated to 1000 ml of LB medium (10 g of pancreatic digests of casein, 5 g of yeast extract, 10 g of sodium chloride) and were incubated for 4 hrs at 37° C. Following the incubation, 1 mM of IPTG (Isopropyl β-D-thiogalactosipyranoside, GibcoBRL cat.# 15529-019) was added in order to induce the expression of lac operon, and then incubated again for 8 hrs to elicit expression of the fusion protein. Next, the cell culture solution was centrifuged at 6,000 rpm for 20 min at 4° C. After removing the supernatant, resultant pellet was dissolved in 10 ml of buffer solution 1 (50 mM of $NaH_2PO_4$, 300 mM of NaCl, 10 mM of Imidazole, at pH 8.0) including 1 mg/ml of lysozyme (Sigma, cat.# L-7651), and was placed on ice for 30 min. Subsequently, ultrasonification (Heat systems, ultrasonic processor XL, with 300 w) for 10 sec and freezing for 10 sec were applied to the solution, repeatedly, until the cumulative time of ultrasonification is 3 min. The eluted solution was centrifuged again at 12,000 rpm for 20 min at 4° C. so as to remove the debris of *E. coli* and isolate pure eluted solution. Then, 2.5 ml of 50% $Ni^{2+}$-NTA agarose slurry (Qiagen, cat# 30230) was added to the isolated solution, and the mixture was stirred at 200 rpm for 1 hr at 4° C. in order to bind fusion protein and $Ni^{2+}$-NTA agarose. The obtained mixture was poured into a column (0.8×4 cm) for chromatography (Bio-Rad, cat.# 731-1550). And the mixture was washed twice with 4 ml of buffer solution 2 (50 mM of $NaH_2PO_4$, 300 mM of NaCl, 20 mM of Imidazole, at pH 8.0). Thereafter, the mixture solution was treated four times with 0.5 ml of buffer solution 3 (50 mM of $NaH_2PO_4$, 300 mM of NaCl, 250 mM of Imidazole, at pH 8.0) to obtain fusion protein fractions. The isolated and purified Mph-1-β-gal fusion protein was subject to SDS-PAGE followed by coomassie blue staining (see FIG. 2). In FIG. 2, the second column corresponds to protein marker for use as a molecular weight standard, and the first column represents fusion protein of Mph-1-β-gal.

Example 3

Transduction of Fusion Protein Across Cell Membrane

Figure 3A:
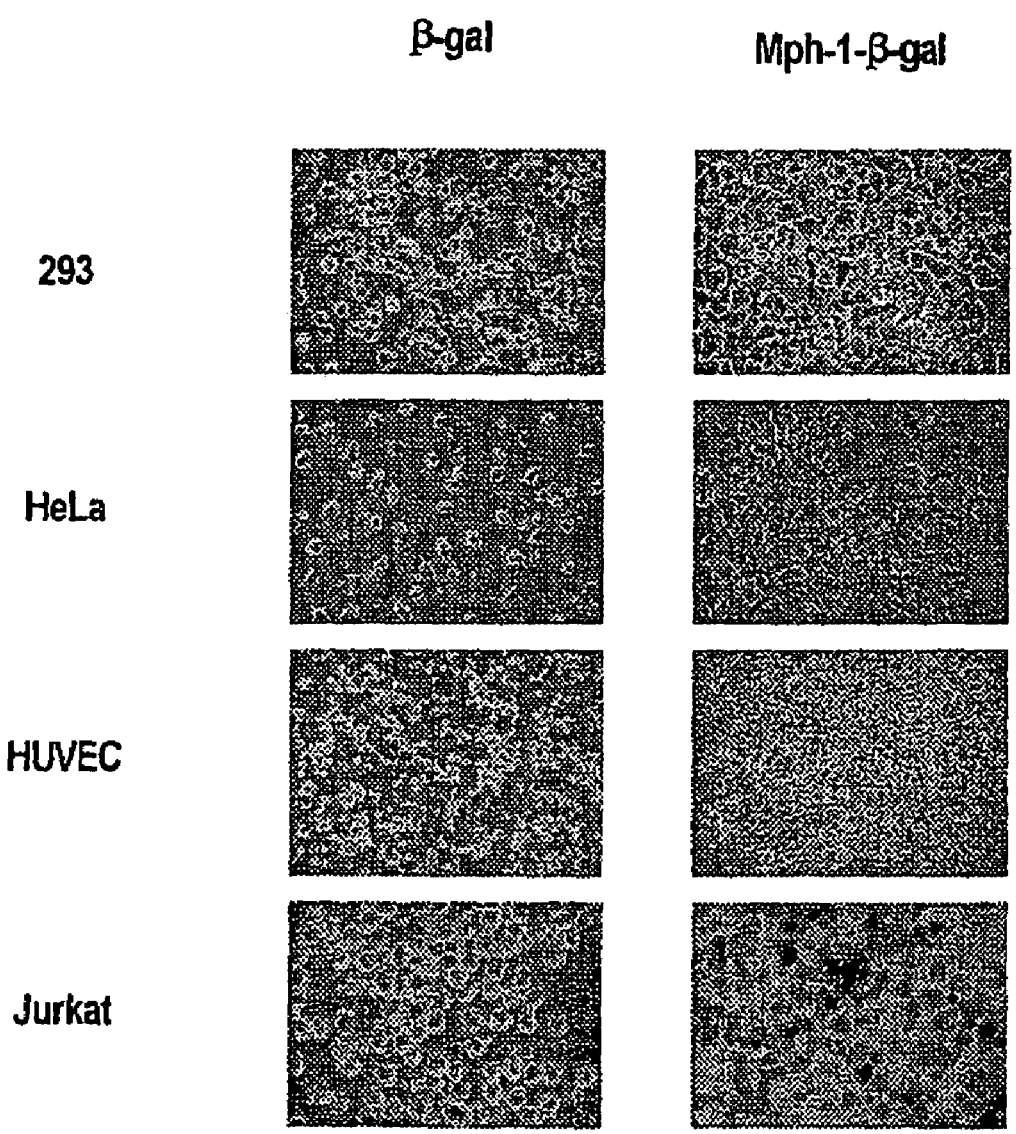
FIG. 3A shows the activity of fusion protein of Mph-1 and β-gal.

HUVEC (ATCC:CRL-1730) (2×10$^5$), HeLa (ATCC:CCL-2) (2×10$^5$), and 293 (ATCC:CRL-1573) (2×10$^5$), which were incubated in 10% FBS (Fetal Bovine Serum) of DMEM, were respectively transferred to Lab-tek II chamber slides. Jurkat cells (ATCC:CRL-10915) (2×10$^5$) incubated in 10% EBS RPMI were transferred to poly-L-lysin coated slides. Each of the slides was treated with the purified 0.5 μM of Mph-1-β-galactosidase for 30 min at 37° C. in 5% $CO_2$ incubator. And the supernatants were removed from the slides. The incubation mixtures were washed using ice-cold PBS four times and then were solidified with 2% formaldehyde solution for 10 min. After removing the solidified solutions, the mixtures were washed again using ice-cold PBS four times. Subsequently, the respective mixtures were treated with 700 μl of β-galactosidase staining solution (Roche. Colo.) for 45 min at 37° C. in 5% $CO_2$ incubator. Following the staining, the mixtures were washed with ice-cold PBS four times after removing the supernatants. Next, the mixtures were mounted with 70% glycerol on the microscope slides. The microscopic photographs were displayed in FIG. 3A. As the results show, Mph-1 fused β-gal was transduced across the cell membranes of the four kinds of cells very efficiently, while β-gal alone was not transduced at all.

Figure 3B:
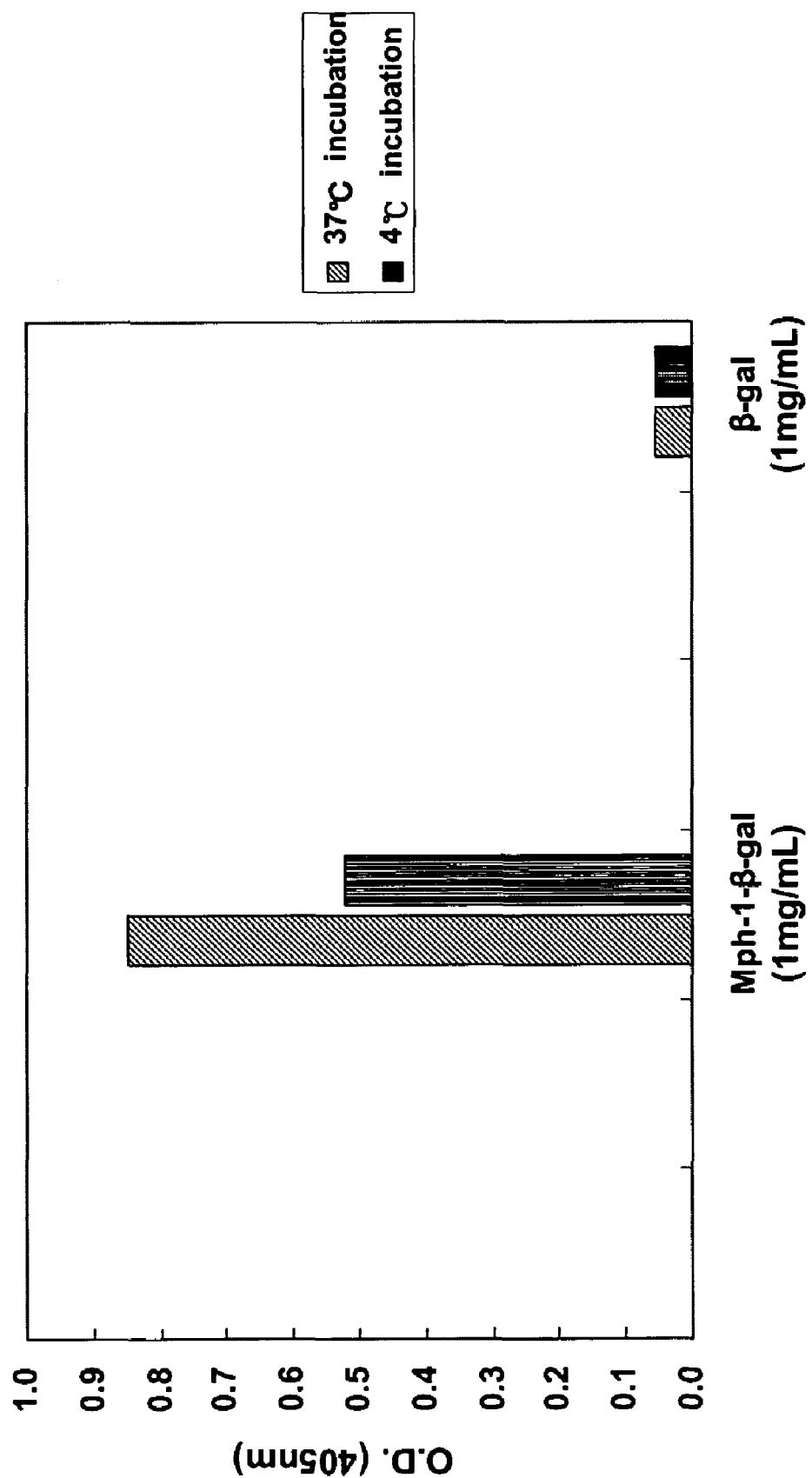
FIG. 3B shows the result of enzyme activity analysis proving that the fusion protein of Mph-1 and β-gal has been effectively transduced into cells.

On the other hand, the transduction of Mph-1-O-gal across cell membrane was detected both at 37° C. and at 4° C., in order to determine whether or not the transduction is carrier-mediated by endocytosis or not. Jurkat cells of 3×10$^6$, which were incubated in 10% FBS (Fetal Bovine Serum) RPMI medium, were washed twice with ice-cold PBS and were suspended in 10% FBS (Fetal Bovine Serum) RPMI medium, and then the soluble fractions of suspension were transferred to 60 min dishes. The suspension was treated with 1 mg/ml of Mph-1-β-galactosidase for 30 min for both at 4° C. and at 37° C. in 5% $CO_2$ incubator. After washing the suspension including Jurkat cells twice with ice-cold PBS, the suspension was dissolved in 1% NP-40 buffer solution (1% NP-40, 150 mM of NaCl, 10 mM of Tris-HCl, 400 μM of EDTA, 1 mM of $Na_3VO_4$, 1 mM of NaF, 10 μg of aprotinin, 10 μg of leupeptin). Then, the solution was centrifuged for 20 min at 4° C., and was quantified using the BCA protein assay reagent kit (PIERCE). Thereafter, 20 μg of sample was mixed with 66 μl of β-galactosidase assay buffer [3 μl of 100×Mg solution, ONPG (o-nitrophenyl-β-D-galactopiranoside)] and 0.1M of sodium phosphate, and then was subjected to reaction for 30 min at 37° C. followed by the addition of 1 M of $Na_2CO_3$ thereto. Absorbance of solution (at 420 nm) was measured three times with microplate reader (Molecular devices), and its mean values and stand deviations were represented in FIG. 3B. As the results show, it was observed that Mph-1-O-gal fusion protein was very efficiently transduced across cell membrane both at 37° C. and at 4° C., which clarified that the protein transduction using the Mph-1 of the present invention did not merely result from receptor-mediated endocytosis or phagocytosis.

Example 4

Comparison of Transduction Efficiencies Across Cell Membrane between Tat and Mph-1

Figure 4A:
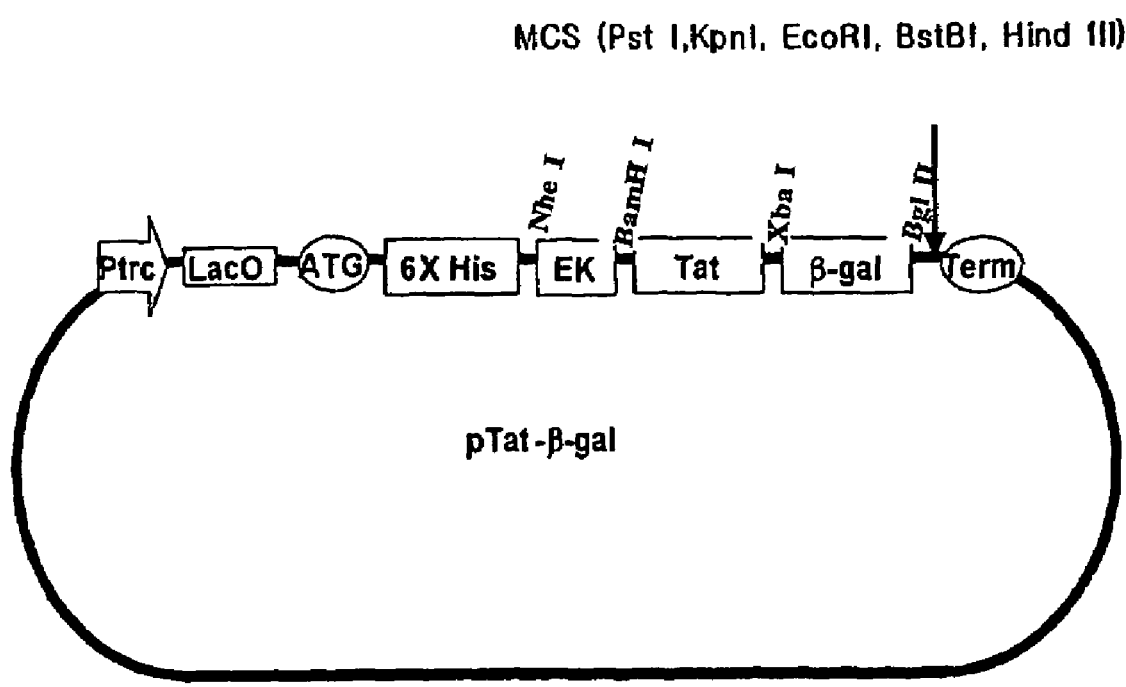
FIG. 4A illustrates the construct of expression vector of pTat-β-gal.
Figure 4B:
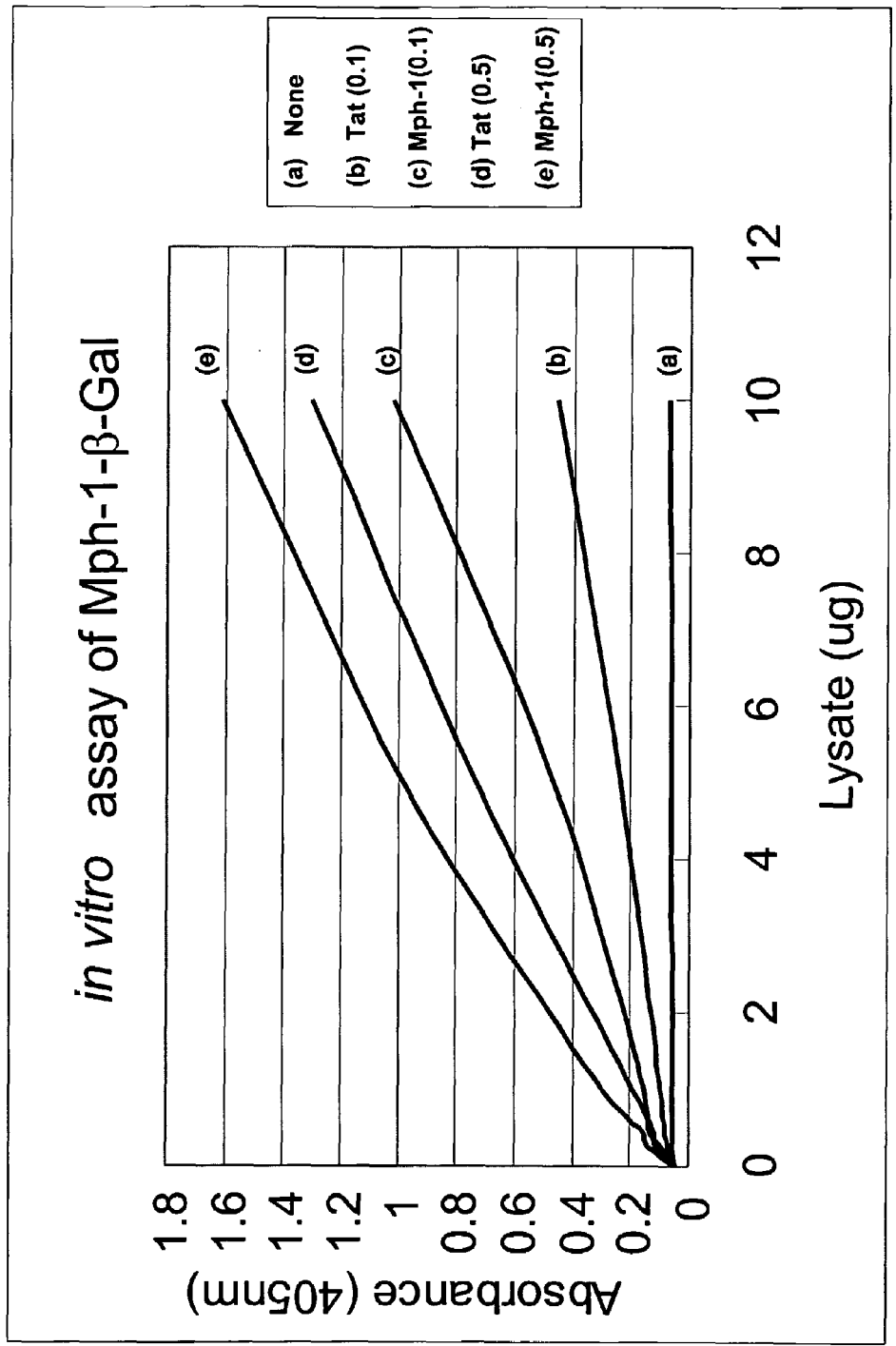
FIG. 4B shows the results of β-gal enzyme activity analysis proving that the fusion protein of Mph-1 and β-gal has been more effectively transduced into the cell than the fusion protein of Tat and β-gal.

A pTat-β-gal DNA construct was designed in order to compare the protein transduction efficiencies across cell membrane between the conventional PTD or Tat and Mph-1 of the present invention. For this purpose, nucleic acid sequence encoding β-galactosidase to be used as a reporter and nucleic acid sequence encoding peptide corresponding to amino acids 47 (Tyrosine)-57 (Arginine) from N-terminus of HIV Tat protein were incorporated. Specifically, a primer of SEQ ID No:4 containing amino acids from 47th of Tyrosine to 57th of Arginine of N-terminus of Mph-1 and BamHI site was synthesized. And PCR amplification was carried out using pIND/lacZ vector (Invitrogen Inc.), which included total genes of β-galactosidase, as a template, and using a primer of SEQ ID NO:3 containing Bgl II site and nucleic acid sequence of 3'-end of β-galactosidase, with pfu turbo DNA polymerase (Stratagene, cat.# 600252-51). The PCR products were cleaved with restriction enzymes of BamHI and BglII, and then purified using Quiaquick PCR purification kit (QIAGEN, cat. # 28104). The purified PCR products were cloned to pTrcHis B (Invitrogen, Cat. No V360-20B), which was purified with gel extraction, at BglII site, and was named as pTat-β-gal. FIG. 4A illustrates the constructs. After isolation and purification of Tat-β-gal fusion protein according to the Example 2, transduction efficiencies of Tat-β-gal and Mph-1-O-gal into cells were compared both at 0.1 ug/ml and at 0.5 ug/ml. As disclosed in FIG. 4B, Mph-1 was transduced into the cells more efficiently both at 0.1 ug/ml and at 0.5 ug/ml. Particularly, the transduction efficiency of Mph-1 was significantly superior when 0.1 ug/ml of fusion protein was introduced.

Example 5

In vivo Transduction of a Desired Protein Using Mph-1

Figure 5A:
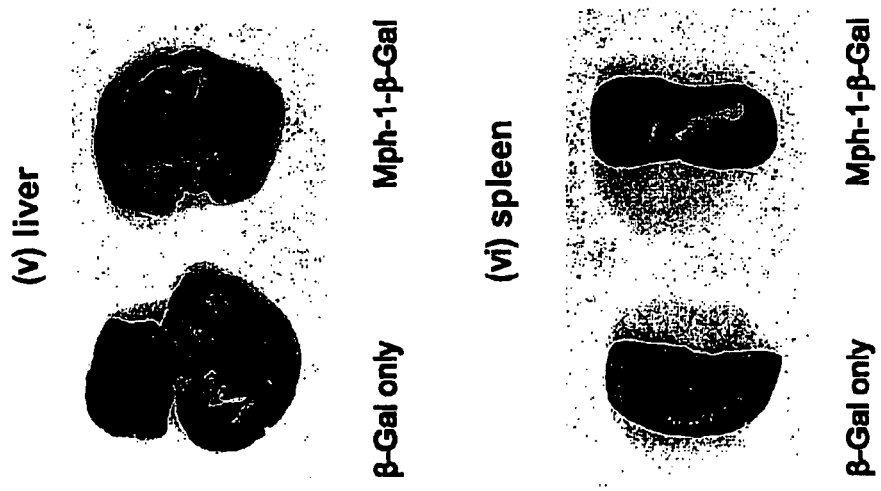
FIG. 5A illustrates the β-gal assay of Mph-1-BTM representing its transducing effects in vivo.
Figure 5A:
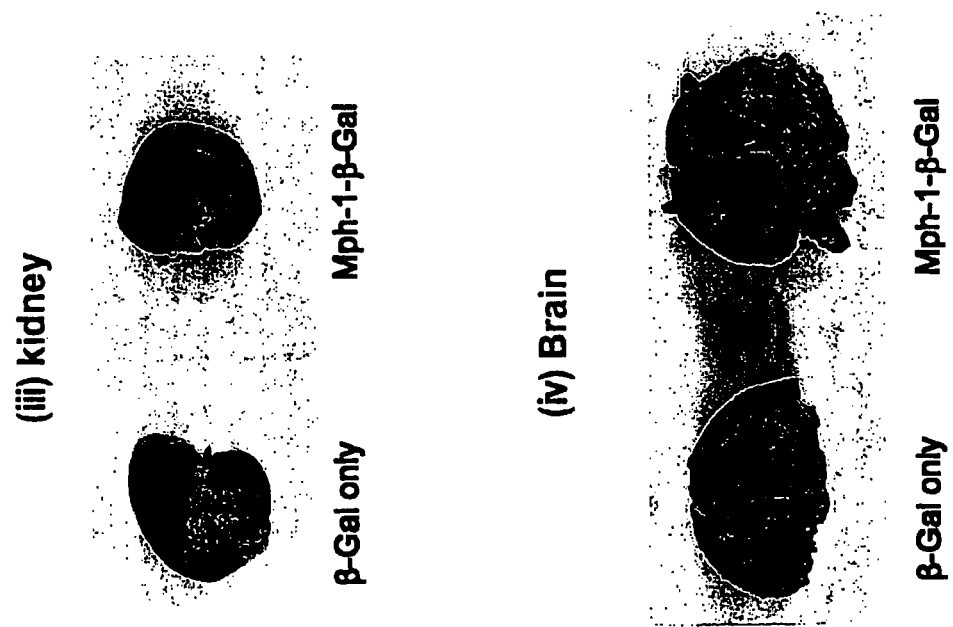

Transduction efficiency of a desired protein using Mph-1 across cell membrane in vivo was detected in this example. In order to detect the efficiency, the isolated and purified 750 ug of Mph-1-β-gal fusion protein of the Example 2 was mixed with PBS, and 500 μl of the mixture was administered by IP (intra peritoneal) injection into 6 months old C57BL/6 mice once a day for 3 days. On the contrary, for the control mice, only the same amount of PBS was administered by IP injection. After 4 hrs from the final injection, the mice were killed and their organs were collected followed by washing with PBS (2 mM of $MgCl_2$). The PBS treated organs were placed on ice-cold 5% formalin. Then, the organs were rinsed with PBS five times, and each of the organs was transferred to β-gal staining solution (Roche. Co.). And, after 12 hrs, the change of color was detected. As disclosed in FIG. 5A, it was observed that β-gal protein was transduced efficiently into kidney, brain, liver, lung and heart, which supported that the target protein was efficiently transferred into organs in vivo using Mph-1-BTM.

Furthermore, it was examined whether the β-gal was transduced by Mph-1-BTM into the cells, which construct the target organs, or was transduced by Mph-1-BTM just to the surface of the organs. In order to carry out this examination, firstly, nucleic acid sequence, which encodes peptide corresponding to amino acids from 858th of Tyrosine to 868th amino acid of Arginine from N-terminus of mouse transcription factor of Mph-1 (genebank code: U63386), and nucleic acid sequence encoding a reporter of eGFP (enhanced Green Fluorescent Protein) were combined. For the combination, a primer of SEQ ID NO:2 containing amino acids from 858th of Tyrosine to 868th amino acid of Arginine from N-terminus of mouse transcription factor of Mph-1 and BamHI site, and a primer of SEQ ID NO:5 containing Bgl II site for cloning and nucleic acid sequence of 3'-terminus of eGFP were synthesized. Then, PCR amplification was carried out using pEGFP-N1 vector (Invitrogen Inc.) comprising total eGFP genes, as a template, with pfu turbo DNA polymerase (Stratagene, cat.# 600252-51).

Figure 5B:
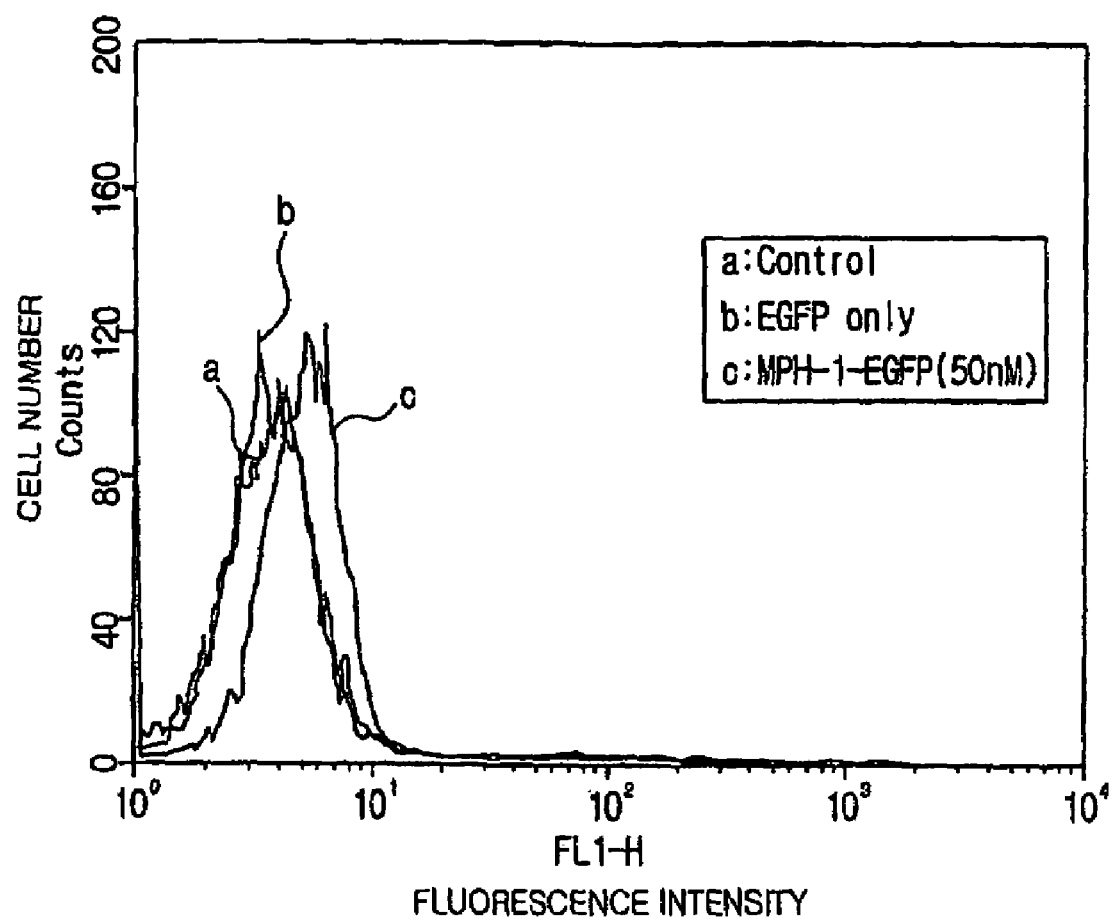
FIG. 5B represents transduction efficiency of eGFP into spleen cell using Mph-1-BTM.

The PCR products were treated with restriction enzymes of BamH I and BglII, and were purified using the Quiaquick PCR purification kit (QIAGEN, cat.# 28104). Next, the purified PCR products were cloned to pTrcHis B (Invitrogen Inc., Cat. No. V360-20B), which was extracted with the gel extraction, at Bgl II site. The obtained recombinant expression vector was named as pMph-1-eGFP. According to Example 2, Mph-1-eGFP, which was expressed in DH5a, was isolated and purified, and then was administered by intraperitoneal injection to the mice. After 4 hrs from the injection, the spleen was removed surgically and was crushed. Splenocytes were isolated from the crushed spleen. Then, FACS analysis was carried out to monitor the eGFP that was transduced into the cells (see FIG. SB). As disclosed in FIG. 5B, it was observed that the eGFP, which was transduced to spleen by Mph-1-BTM, was also transduced efficiently to the splenocytes that constructs the spleen.

Figure 5C:
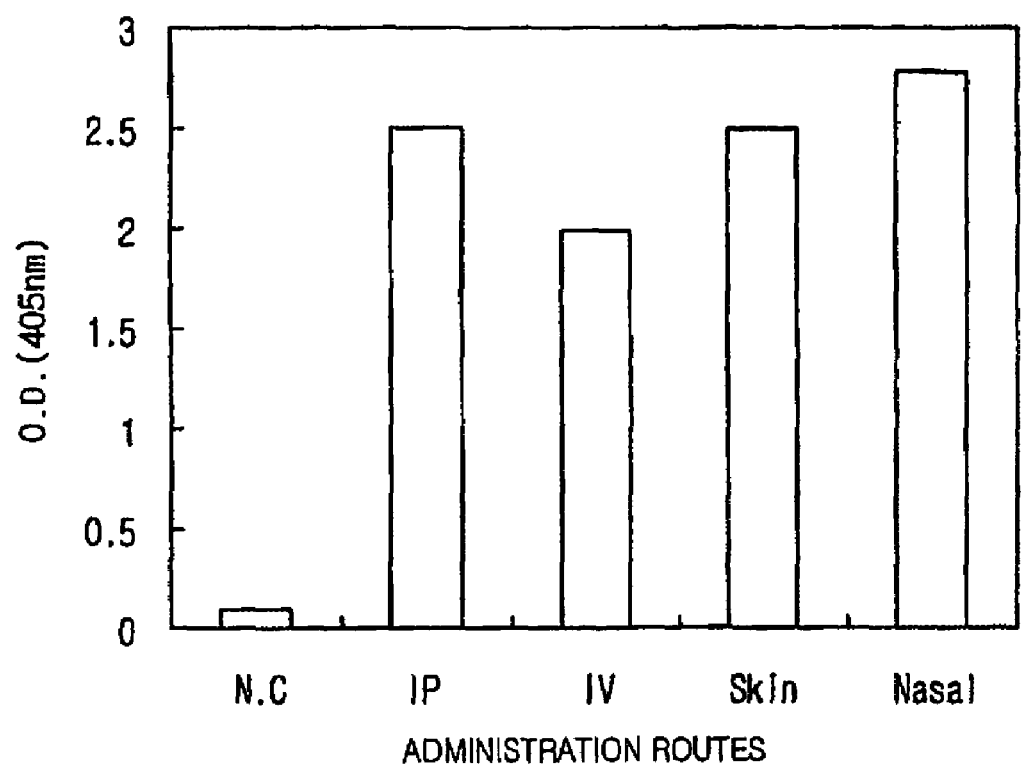
FIG. 5C represents the transduction of β-gal into T cells in blood via numerous administration routes. N.C. stands for negative control.

Furthermore, it was examined that the desired protein was transduced by Mph-1-BTM to organs in vivo via blood. 500 μl of the mixture of the isolated and purified 750 μg of Mph-1-β-gal fusion protein and PBS was administered to 6 months old C57BL/6 mouse once a day for three days by I.P. (intraperitoneal), IV (intravenous), SC (subcutaneous) or nasal route. Whereas, the control mice were given the same amount of PBS alone by I.P. After collecting blood from mouse injected with the fusion proteins, T cells were isolated using MACS and anti-CD3 mAb, and then the activity of 3-galactosodase was detected as disclosed in the Example 3. The results are displayed in FIG. 5C. As the results show, the fusion proteins were administered efficiently by the Mph-1-BTM through numerous administration routes, such as IP, IV, SC and nasal routes, to the T cells in blood.

Example 6

Intracellular Transduction of DNA (CD8-ζ) Using Mph-1-BTM (STEP 1) Preparation of Expression Vector Including Fusion Genes of Mph-1 and Gal4

Figure 6:
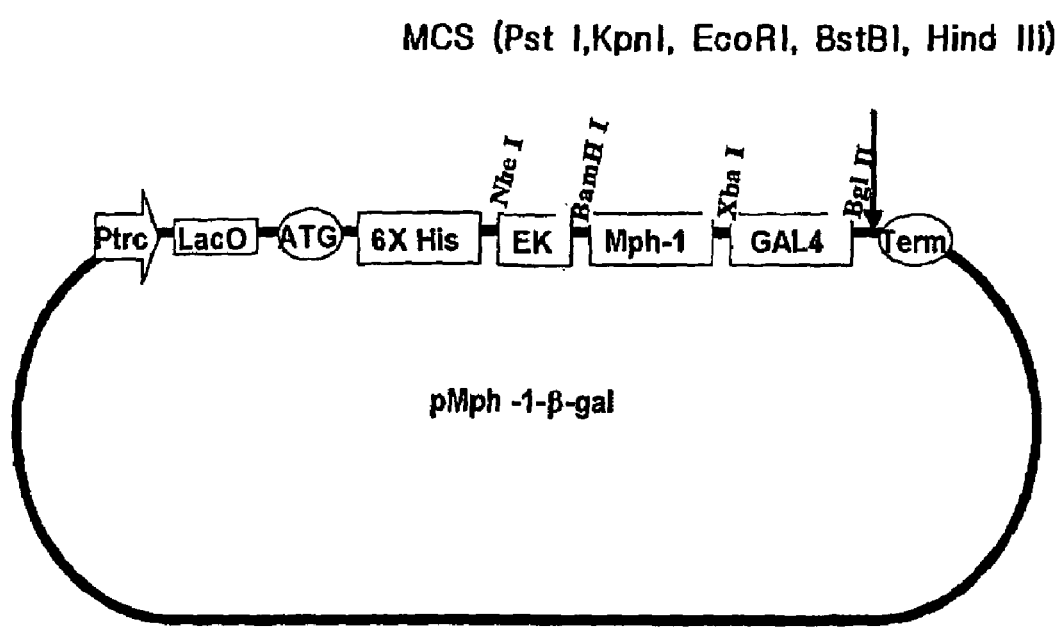
FIG. 6 illustrates the construct of recombinant expression vector of pMph-1-Gal4.

The pMph-1-β-gal vector of the Example 1 was treated with restriction enzymes, Xba I and Bgl II, to remove β-galactosidase gene therefrom. Then, pMph-1-Gal4 plasmid was developed by carrying out conventional PCR amplification and molecular cloning, as disclosed in the Example 1, using a primer of SEQ ID NO:8 having N-terminal sequence of GAL4 DNA binding protein and Xba I restriction enzyme site, and a primer of SEQ ID NO:9 having N-terminal sequence of GAL4 DNA binding protein and Bgl II restriction enzyme site. FIG. 6 illustrates the construct of the expression vector of pMph-1-Gal4.

Figure 7:
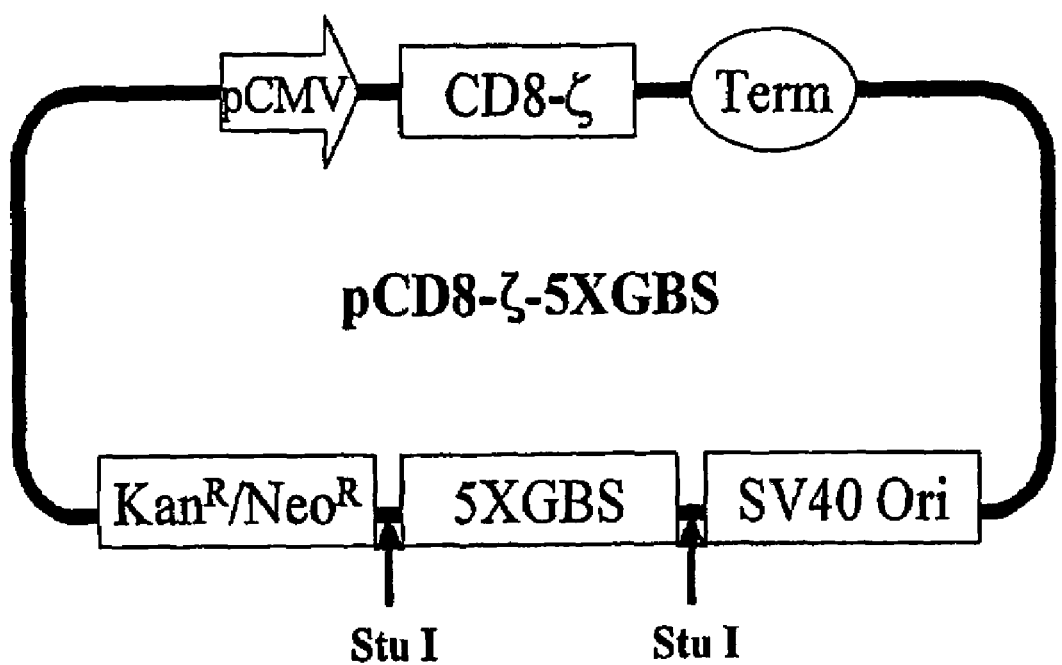
FIG. 7 illustrates the construct of recombinant expression vector of pCD8-ζ-5×GBS (Gal4 binding sequence).
Figure 12:
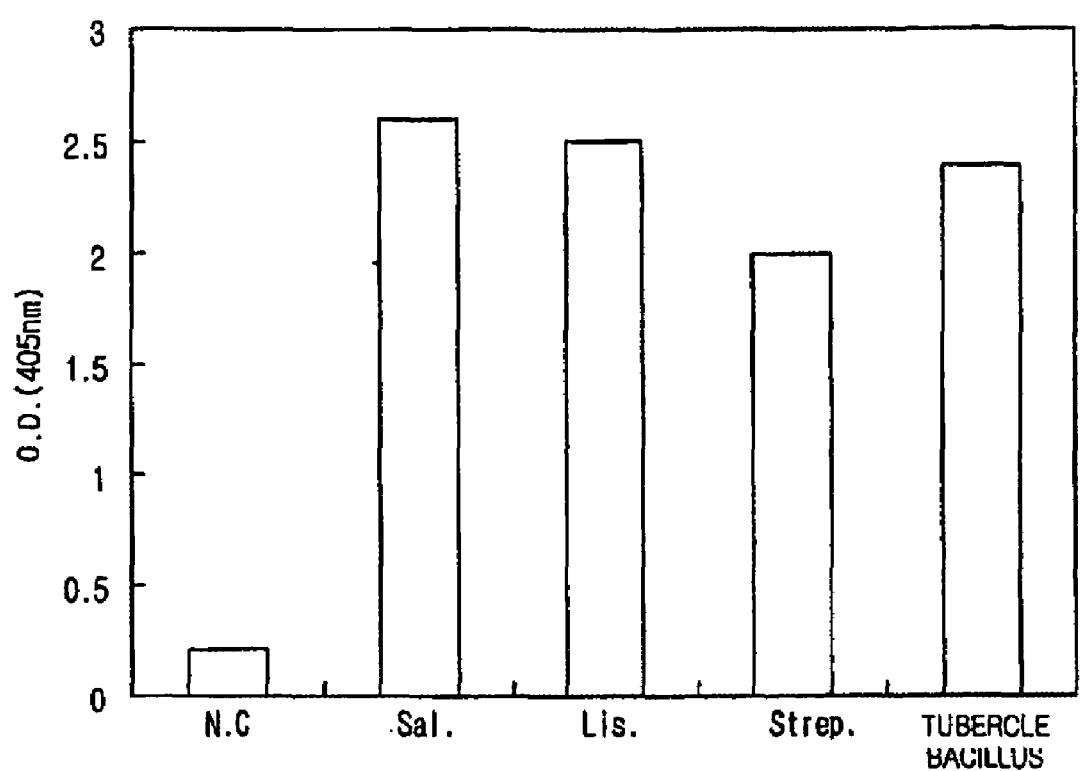
FIG. 12 represents the transduction of β-gal proteins into bacteria, *salmonella, Streptococcus*, and tuberculous *bacillus* using Mph-1-BTM. N.C. stands for negative control.

(STEP 2) Preparation of Expression Vector of pCD8-z-5× GBS Having DNA Sequence to which Gal4 DNA Binding Protein Binds Specifically In order for the binding of Mph-1-Gal4 of the Example 1 to be carried out more efficiently, pCD8-z-5XGBS was designed by cloning 5 (five) successive GBS sequences at the StuI restriction enzyme recognition site of pcDNA3-CD8-z, which was prepared by inserting CD8-ζ into pcDNA3 expression vector (Invitrogen Inc.) at restriction enzyme recognition sites for XbaI and BamHI. Specifically, nucleic acid sequence corresponding to GBS was synthesized using a primer and hybridized, and then was cloned to pCD8-ζ at StuI recognition site of 3' terminus. FIG. 7 illustrates the structure of expression vector of pCD8-ζ-5XGBS. The nucleic acid sequence of GBS was designated as SEQ ID NO:10.

(STEP 3) Confirmation of the Transduction of CD8-ζDNA Using Mph-1

Gal4s of Mph-1-Gal4 fusion proteins were respectively bound to each of the five GBSs of pCD8-ζ-5×GBS. The expressed and purified Mph-1-Gal4 fusion protein in the Example 2 was bound to pCD8-ζ-5×GBS DNA prepared in the step 2 using the expression vector of pMph-1-Gal4 manufactured in the step 1 at room temperature. After mixing the fusion complex with PBS, the mixture was introduced to 10⁷ of primary T cells, and then was incubated for 48 hrs at 37° C. in order to induce over-expression of CD8-ζ fusion proteins elicited by DNA constructs delivered into the cells. In order to determine the over-expression of CD8-ζ fusion protein on the cell surface, FACS (Fluorescence-Activated Cell Sorter) analysis was carried out using OKT8 (ATCC No. CRL-8014) of a monoclonal antibody to CD8 (Current Protocol for Immunology). FIG. 8A discloses the results. As shown in FIG. 8A, CD8-ζ fused with Mph-1 biomolecule transduction peptide was transduced into the cells across the cell membrane. As negative controls, the expression of CD8-ζ chimeric molecules in T cells, which include Mph-1-Gal4 fusion proteins not having pCD8-ζ-5×GBS or including pCD8-ζ-5× GBS alone, were analyzed using FACS. As the results, the desired DNA construct to be transduced into the cell was bound to binding sequences of DNA binding protein, thereby the DNA binding protein fused to Mph-1 efficiently transferred the desired DNA construct across the cell membrane for the expression of the DNA construct.

In addition, in this example, the transduction of DNA using Mph-1-BTM was examined in vivo. For this purpose, a complex between Mph-1-Gal4 fusion protein, which was fused at room temperature, and pCD8-ζ-5XGBS was administered by I.P. injection into a mouse, and then, after 48 hrs from the injection, T cells in blood were collected using T cell specific anti-CD2 mAb and MACS, as disclosed in the Example 5. Thereafter, splenocytes of spleen were isolated, and the level of expression of CD8-ζ chimeric proteins on the surface of the splenocytes was detected with FACS. The results are displayed in FIG. 8B. As the results show, the expression vector of pCD8-ζ-5XGBS, which was transduced in vivo into the cell using Mph-1-BTM and Gal4, was effectively transduced not only into T cells but also into splenocytes of the spleen.

Example 7

Immunosuppressive Effects In Vivo of Mph-1-zA1A2 and Mph-1-CTLA-4 Protein Drugs

As confirmed in the example disclosed above, it was proved that Mph-1-BTM can efficiently transfer numerous materials, which control in vivo various physiological responses, such as proteins, DNA and/or RNA and chemical compounds, into numerous organs or cells constructing the organs by binding the materials covalently or non-covalently. Thus, in this example, a new type of protein drug, which could regulate immune response in vivo, was provided by introducing wild type or mutant protein that regulated intracellular signal transduction, using the Mph-1-BTM. As a desired protein inhibiting immune response elicited by T cell, cytoplasmic domain of z chain of a signal transduction chain of TcR complex, which recognizes in vivo both a portion of antigenic peptide and MHC, thereby transfers activation signal into the cells, was selected in this example. We verified in the preliminary study the fact that when over-expressing zA1A2 type, which was prepared by substituting Tyrosine with Phenylalanine at 1$^{st}$ ITAM of cytoplasmic domain of TCR z chain, the T cell activation signals were significantly blocked (Wook-Jin Chae et al., JBC (2003)). Based on such results, an expression vector was prepared by fusing Mph-1-BTM and zA1A2 type of TcR z chain. FIG. 9A illustrates the construct. In order to make this expression vector, a 5' primer of SEQ ID NO:13 comprising nucleic acid sequence of Xba I restriction enzyme, nucleic acid sequence of Mph-1-BTM and N-terminal nucleic acid sequence of cytoplasmic domain, and a 3' primer of SEQ ID NO:13 comprising nucleic acid sequence of Hind III site and C-terminal nucleic acid sequence of z chain were prepared. Then, PCR amplification was carried out using pcDNA3-zA1A2 expression vector synthesized in our laboratory (Wook-Jin Chae et al., JBC (2003)), as a template, and using the primers above mentioned. Subsequently, the PCR products were cloned to an expression vector of pGELysRS(2) both at Xba I and Hind III sites, wherein the pGELysRS(2) vector was manufactured by deleting Xba I restriction enzyme at 5' region of ATG-LysRS of an expression vector, pGELysRS, that effectively expresses a protein in soluble type. Thereby, pMph-1-2-zA1A2 expression vector was developed.

In order to prepare another desired protein, which regulates in vivo immune response, using Mph-1-BTM, cytoplasmic domain of CTLA-4 protein, which is a negative regulator during the T cell activation process, was employed as a fusion partner to the Mph-1-BTM. The CTLA-4 is a cell membrane protein found on the surface of activated T cell, and it is known to inhibit T cell activation by binding any one of proteins of B7 family on the surface of APC (Antigen Presenting Cell). In order to prepare a fusion protein of Mph-1-BTM and cytoplasmic domain of CTLA-4, an expression vector of pMph-1-CTLA-4 was designed, and its construct was displayed in FIG. 9B. In order to make this expression vector, a 5' primer of SEQ ID NO:15 comprising nucleic acid sequence of Xba I restriction enzyme, nucleic acid sequence of Mph-1-BTM and N-terminal nucleic acid sequence of CTLA-4 protein, and a 3' primer of SEQ ID NO:13 comprising nucleic acid sequence of Hind III and C-terminal nucleic acid sequence of CTLA-4 were prepared. Then, PCR amplification was carried out using primary T cell cDNA mixture synthesized in our laboratory (Wook-Jin Chae et al., JBC (2003)), as a template, and using the primers above mentioned. Subsequently, the PCR products were cloned to an expression vector of pGELysRS(2) both at Xba I and Hind III sites, wherein the pGELysRS(2) vector was generated by deleting Xba I restriction enzyme at 5' region of ATG-LysRS of an expression vector, pGELysRS, that effectively expresses a protein in soluble type. Thus, pMph-1-CTLA-4 expression vector was developed.

Using the prepared pMph-1-zA1A2 and pMph-1-CTLA-4 expression vectors, E. coli of BL21 (Invitrogen, cat. no.: c7010-03) was transformed by heat shock transformation. After isolating and purifying the expressed fusion proteins, the obtained products were subject to SDS-PAGE followed by coomasie blue staining. FIG. 10A and B represent the results. With the isolated and purified Mph-1-zA1A2 fusion protein and Mph-1-CTLA-4 fusion protein, immunosuppressive effects in vivo were examined and analyzed using the organ rejection animal models of rat heterocardiac allograft as disclosed in the Example 9 (Jae-Hyuck Sim et al., *PNAS* 9(16):10617-10622 (2002)). The results are represented in Table 2.

TABLE 2

| Drugs | Concentration (mg/kg) | Adimini-stration | Days of alive | Rat number |
|---|---|---|---|---|
| Cremophor | 5 | I.P. | 9 | 4 |
| | 5 | I.P. | 10 | 3 |
| CyclosporinA/Cremophor | 5 | I.P. | >100 | 2 |
| Mph-1-zA1A2/PBS | 0.05 | I.P. | >160 | 8 |
| Mph-1-CTLA-4/PBS | 0.05 | I.P. | >160 | 12 |

As the results, the transplanted organs in the organ rejection animal models, which were respectively given Mph-1-zA1A2 and Mph-1-CTLA-4 by IP injection (0.05 ug/mi) or by subcutaneous administration (0.04 ug/ml), operated 160 days or more, while the transplanted organs in the organ rejection animal models, which were given conventional inimunosuppressor of CsA (cyclosphorin A) by IP injection, operated 100 days or more. On the other hand, the transplanted organs in the organ rejection animal models, which were given cremophor by IP injection, operated only 9 or 10 days. These results suggested that both of zA1A2 type of TCR z chain and CTLA-4 were efficiently transduced into the T cells by Mph-1-BTM and inhibited T cell activation to represent immunosuppressive effects.

Example 8

Transduction of Macromolecules into Plant Callus Cells Using Mph-1-BTM

The desired proteins were transduced into non-animal cells using Mph-1-BTM in this example. Briefly, cultured plant callus cells were given 10 μM of Mph-1-β-gal fusion proteins, and, after 1 hr, the cells were examined under confocal microscope in order to analyze the transduction level of β-galactosidase into the cells. The results were displayed in FIG. 11. Specifically, collected tobacco leaves were cultured in callus inducing medium including auxin and cytokine, and the produced plant callus was cultured in agar free MS medium (suspension culture). As the results show, after 15 min from the introduction of fusion protein using Mph-1-BTM it was observed that β-galactosidase was effectively transduced not only into the callus cells but also into the nucleus of the cells.

Example 9

Transduction of Macromolecules into Various Kinds of Bacteria by Mph-1-BTM

The desired proteins were transduced into various kinds of bacteria in this example. 1 μM of Mph-1-β-gal fusion proteins was introduced to various bacteria, such as *Salmonella typhymurium, Listeria monocytogenes, Streptococcus aureus* and *tubercle bacillus*. After 1 hr from the introduction, the activities of the transduced β-galactosidase were detected and the results were shown in FIG. 12. As the results show, it was confirmed that macromolecules were efficiently transduced into the bacterial cells with Mph-1-BTM.

INDUSTRIAL APPLICABILITY

As disclosed above, Mph-1-BTM of the present invention, which includes the amino acid sequence of SEQ ID NO:1, delivers biologically active functional regulatory molecules in vivo and in vitro into the cytosol, organelles or nucleus of prokaryotic and eukaryotic cells, via numerous paths, for example, intramuscular, intraperitoneal, intravein, oral, nasal, subcutaneous, intradermal, mucosal, and inhalation. Thus, this invention can be used to provide protein drugs, recombinant vaccines, DNA/RNA vaccines, and functional genes. Furthermore, this invention can be used to provide novel methods for treating disease using protein, genes, chemical compounds. Furthermore, this invention can be used to provide novel drug delivery system and proteins having natural structure and functions.

What is claimed is:

1. A biomolecule transduction motif (BTM) consisting of the amino acid sequence of SEQ ID NO:1.

2. A biomolecule transduction complex (BTC) comprising a macromolecule and a BTM comprising the amino acid sequence of SEQ ID NO:1, wherein the macromolecule is selected from the group consisting of:
   (i) a nucleic acid;
   (ii) a carbohydrate;
   (iii) a lipid; and
   (iv) a chemical compound.

3. The biomolecule transduction complex (BTC) of claim 2, wherein the macromolecule is a chemical compound.

4. A method of transducing the biomolecule transduction complex (BTC) of claim 2 in vivo or in vitro into a prokaryotic or eukaryotic cell, comprising contacting a prokaryotic or eukaryotic cell with said BTC.

5. The method of claim 4, wherein the biomolecule transduction complex (BTC) is transduced in vivo into a mammal, comprising administering the BTC intramuscularly, intraperitoneally, intravenously, orally, nasally, subcutaneously, intradermally, mucosally or by inhalation.

6. The method of claim 4, wherein the biomolecule transduction complex (BTC) is transduced in vitro into a prokaryotic cell, comprising contacting the prokaryotic cell with said BTC.

7. The method of claim 6, wherein the cell is a bacterial cell.

8. The method of claim 7, wherein the bacterial cell is selected from the group consisting of: *Salmonella typhymurium, Listeria monocytogenes, Streptococcus aureus*, and *tubercle bacillus*.

9. An isolated polynucleotide comprising a first nucleic acid sequence encoding SEQ ID NO:1 and a second nucleic acid sequence encoding a protein, wherein the protein is selected from the group consisting of:
   (i) CD8-ζ;
   (ii) Gal4;
   (iii) eGFP;
   (iv) zA1A2; and
   (v) CTLA-4.

10. The isolated polynucleotide of claim 9, further comprising the nucleic acid sequence of SEQ ID NO:10.

11. The method of claim 4, wherein the biomolecule transduction complex (BTC) is transduced in vitro into a eukaryotic cell, comprising contacting the eukaryotic cell with said BTC.

12. The method of claim 11, wherein the cell is selected from the group consisting of:
   (i) a HUVEC cell;
   (ii) a Hela cell;
   (iii) a 293 cell;
   (iv) a Jurkat cell; and
   (v) a plant callus cell.

13. The biomolecule transduction complex (BTC) of claim 2, wherein the macromolecule is a nucleic acid.

14. The biomolecule transduction complex (BTC) of claim 13, wherein the nucleic acid encodes a cytokine selected from the group consisting of: interleukin-2, interleukin-4, interleukin-12, gamma-interferon, chemokine and EGF.

15. The biomolecule transduction complex (BTC) of claim 2, wherein the macromolecule is a carbohydrate.

16. The biomolecule transduction complex (BTC) of claim 2, wherein the macromolecule is a lipid.

17. A method of transducing the BTM of claim 1 in vivo or in vitro into a prokaryotic or eukaryotic cell, comprising contacting a prokaryotic or eukaryotic cell with said BTM.

18. The method of claim 17, wherein the BTM is fused to a protein.

19. The method of claim 18, wherein the protein is selected from the group consisting of: β-galactosidase, enhanced Green Fluorescent Protein (eGFP), zA1A2, CTLA-4, and CD8-ζ.

20. A method of transducing a biomolecule transduction motif (BTM) in vivo or in vitro into a prokaryotic or eukaryotic cell, comprising contacting a prokaryotic or eukaryotic cell with a BTM comprising the amino acid sequence of SEQ ID NO:1.

21. The method of claim 20, wherein the BTM is fused to a protein.

22. The method of claim 21, wherein the protein is selected from the group consisting of: β-galactosidase, enhanced Green Fluorescent Protein (eGFP), zA1A2, CTLA-4, and CD8-ζ.

* * * * *

SEQUENCE LISTING

```
<160> NUMBER OF SEQ ID NOS: 22

<210> SEQ ID NO 1
<211> LENGTH: 11
<212> TYPE: PRT
<213> ORGANISM: Artificial Sequence
<220> FEATURE:
<223> OTHER INFORMATION: Biomolecule transduction motif

<400> SEQUENCE: 1

Tyr Ala Arg Val Arg Arg Arg Gly Pro Arg Arg
  1               5                  10

<210> SEQ ID NO 2
<211> LENGTH: 72
<212> TYPE: DNA
<213> ORGANISM: Artificial Sequence
<220> FEATURE:
<223> OTHER INFORMATION: 5 primer for Mph-1
<220> FEATURE:
```

```
<221> NAME/KEY: misc_feature
<222> LOCATION: (4)..(9)
<223> OTHER INFORMATION: BamHI site
<220> FEATURE:
<221> NAME/KEY: misc_feature
<222> LOCATION: (43)..(48)
<223> OTHER INFORMATION: XbaI site

<400> SEQUENCE: 2
cgcggatcct atgcacgtgt tcggaggcgt ggaccccgcc gctctagaga tcccgtcgtt    60
ttacaacgtg ac                                                       72

<210> SEQ ID NO 3
<211> LENGTH: 26
<212> TYPE: DNA
<213> ORGANISM: Artificial Sequence
<220> FEATURE:
<223> OTHER INFORMATION: 3 primer for beta-gal
<220> FEATURE:
<221> NAME/KEY: misc_feature
<222> LOCATION: (3)..(8)
<223> OTHER INFORMATION: BglII site

<400> SEQUENCE: 3
gaagatcttt atttttgaca ccagac                                        26

<210> SEQ ID NO 4
<211> LENGTH: 75
<212> TYPE: DNA
<213> ORGANISM: Artificial Sequence
<220> FEATURE:
<223> OTHER INFORMATION: 5 primer for tat
<220> FEATURE:
<221> NAME/KEY: misc_feature
<222> LOCATION: (4)..(9)
<223> OTHER INFORMATION: BamHI site

<400> SEQUENCE: 4
cgcggatcct atggaaggaa gaagaagcgg agacaaagac gacgatctag agatcccgtc    60
gttttacaac gtgac                                                    75

<210> SEQ ID NO 5
<211> LENGTH: 18
<212> TYPE: DNA
<213> ORGANISM: Artificial Sequence
<220> FEATURE:
<223> OTHER INFORMATION: 3 primer for eGFP
<220> FEATURE:
<221> NAME/KEY: misc_feature
<222> LOCATION: (3)..(8)
<223> OTHER INFORMATION: BglII site

<400> SEQUENCE: 5
gaagatcttt tacttgta                                                 18

<210> SEQ ID NO 6
<211> LENGTH: 18
<212> TYPE: DNA
<213> ORGANISM: Artificial Sequence
<220> FEATURE:
<223> OTHER INFORMATION: 5 primer for B7.1
<220> FEATURE:
<221> NAME/KEY: misc_feature
<222> LOCATION: (4)..(9)
<223> OTHER INFORMATION: BamHI site

<400> SEQUENCE: 6
cgcggatccg gccacaca                                                 18
```

<210> SEQ ID NO 7
<211> LENGTH: 18
<212> TYPE: DNA
<213> ORGANISM: Artificial Sequence
<220> FEATURE:
<223> OTHER INFORMATION: 3 primer for B7.1
<220> FEATURE:
<221> NAME/KEY: misc_feature
<222> LOCATION: (3)..(8)
<223> OTHER INFORMATION: BglII site

<400> SEQUENCE: 7
gaagatcttt acagggcg                                                 18

<210> SEQ ID NO 8
<211> LENGTH: 21
<212> TYPE: DNA
<213> ORGANISM: Artificial Sequence
<220> FEATURE:
<223> OTHER INFORMATION: 5 primer for Gal4
<220> FEATURE:
<221> NAME/KEY: misc_feature
<222> LOCATION: (4)..(9)
<223> OTHER INFORMATION: XbaI site

<400> SEQUENCE: 8
cgctctagaa agctactgtc t                                             21

<210> SEQ ID NO 9
<211> LENGTH: 21
<212> TYPE: DNA
<213> ORGANISM: Artificial Sequence
<220> FEATURE:
<223> OTHER INFORMATION: 3 primer for Gal4
<220> FEATURE:
<221> NAME/KEY: misc_feature
<222> LOCATION: (4)..(9)
<223> OTHER INFORMATION: HindIII site

<400> SEQUENCE: 9
cccaagcttc ggcgatacag t                                             21

<210> SEQ ID NO 10
<211> LENGTH: 119
<212> TYPE: DNA
<213> ORGANISM: Artificial Sequence
<220> FEATURE:
<223> OTHER INFORMATION: Gal4 binding sequence

<400> SEQUENCE: 10
ctcgaggaca gtactccgct cggaggacag tactccgatc cgtcgactct agagggtata      60
taatgcgcca gctcgaattc atcagcttgg cgagattttc aggagctaag gaagctaaa     119

<210> SEQ ID NO 11
<211> LENGTH: 51
<212> TYPE: DNA
<213> ORGANISM: Artificial Sequence
<220> FEATURE:
<223> OTHER INFORMATION: N teminal of BamHI-Mph-1-B7
<220> FEATURE:
<221> NAME/KEY: misc_feature
<222> LOCATION: (3)..(9)
<223> OTHER INFORMATION: BamHI site

<400> SEQUENCE: 11
cgcggatcct atgcacgtgt tcggaggcgt ggaccccgcc gcggccacac a               51

```
<210> SEQ ID NO 12
<211> LENGTH: 18
<212> TYPE: DNA
<213> ORGANISM: Artificial Sequence
<220> FEATURE:
<223> OTHER INFORMATION: C terminal of BgIII and B7
<220> FEATURE:
<221> NAME/KEY: misc_feature
<222> LOCATION: (3)..(8)
<223> OTHER INFORMATION: BglII site

<400> SEQUENCE: 12
gaagatcttt acagggcg                                                 18

<210> SEQ ID NO 13
<211> LENGTH: 87
<212> TYPE: DNA
<213> ORGANISM: Artificial Sequence
<220> FEATURE:
<223> OTHER INFORMATION: 5 primer for Mph-1-A1A2
<220> FEATURE:
<221> NAME/KEY: misc_feature
<222> LOCATION: (4)..(9)
<223> OTHER INFORMATION: BamHI site

<400> SEQUENCE: 13
cgcggatcct atgcacgtgt tcggaggcgt ggaccccgcc gcgggtctag attcctgaga   60
gtgaagttca gcaggagcgc agagccc                                       87

<210> SEQ ID NO 14
<211> LENGTH: 72
<212> TYPE: DNA
<213> ORGANISM: Artificial Sequence
<220> FEATURE:
<223> OTHER INFORMATION: 3 primer for Mph-1-A1A2
<220> FEATURE:
<221> NAME/KEY: misc_feature
<222> LOCATION: (4)..(9)
<223> OTHER INFORMATION: HindIII site

<400> SEQUENCE: 14
cccaagcttc ttgtcatagt cgtccttgta gtcgcggccg ccgcgagggg gcagggcctg   60
catgtgaagg gc                                                       72

<210> SEQ ID NO 15
<211> LENGTH: 75
<212> TYPE: DNA
<213> ORGANISM: Artificial Sequence
<220> FEATURE:
<223> OTHER INFORMATION: 5 primer for Mph-1-CTLA4
<220> FEATURE:
<221> NAME/KEY: misc_feature
<222> LOCATION: (4)..(9)
<223> OTHER INFORMATION: BamHI site

<400> SEQUENCE: 15
cgcggatcct atgcacgtgt tcggaggcgt ggaccccgcc gcgggtctag aaaaatgcta   60
aagaaaagaa gccct                                                    75

<210> SEQ ID NO 16
<211> LENGTH: 72
<212> TYPE: DNA
<213> ORGANISM: Artificial Sequence
<220> FEATURE:
<223> OTHER INFORMATION: 3 primer for Mph-1-CTLA4
<220> FEATURE:
<221> NAME/KEY: misc_feature
```

```
<222> LOCATION: (4)..(9)
<223> OTHER INFORMATION: HindIII site

<400> SEQUENCE: 16
cccaagcttc ttgtcatagt cgtccttgta gtcgcggccg ccattgatgg gaataaaata    60
aggctgaaat tg                                                        72

<210> SEQ ID NO 17
<211> LENGTH: 73
<212> TYPE: DNA
<213> ORGANISM: Artificial Sequence
<220> FEATURE:
<223> OTHER INFORMATION: 5 primer for Mph-1-insulin
<220> FEATURE:
<221> NAME/KEY: misc_feature
<222> LOCATION: (3)..(9)
<223> OTHER INFORMATION: BamHI site

<400> SEQUENCE: 17
cgcggatcct atgcacgtgt tcggaggcgt ggaccccgcc gcgggcaggg ttccagggtg    60
gctggacccc agg                                                       73

<210> SEQ ID NO 18
<211> LENGTH: 77
<212> TYPE: DNA
<213> ORGANISM: Artificial Sequence
<220> FEATURE:
<223> OTHER INFORMATION: 3 primer for Mph-1-insulin
<220> FEATURE:
<221> NAME/KEY: misc_feature
<222> LOCATION: (4)..(9)
<223> OTHER INFORMATION: HindIII site

<400> SEQUENCE: 18
cccaagcttc ttgtcatagt cgtccttgta gtcgcggccg cgctggttca agggctttat    60
tccatctctc tcggtgc                                                   77

<210> SEQ ID NO 19
<211> LENGTH: 11
<212> TYPE: PRT
<213> ORGANISM: Artificial Sequence
<220> FEATURE:
<223> OTHER INFORMATION: protein transduction domain

<400> SEQUENCE: 19

Tyr Gly Arg Lys Lys Arg Arg Gln Arg Arg Arg
 1               5                  10

<210> SEQ ID NO 20
<211> LENGTH: 5
<212> TYPE: PRT
<213> ORGANISM: Artificial Sequence
<220> FEATURE:
<223> OTHER INFORMATION: biomolecule transduction peptide

<400> SEQUENCE: 20

Asp Asp Asp Asp Lys
 1               5

<210> SEQ ID NO 21
<211> LENGTH: 7
<212> TYPE: PRT
<213> ORGANISM: Artificial Sequence
<220> FEATURE:
<223> OTHER INFORMATION: biomolecule transduction peptide
```

```
-continued

<400> SEQUENCE: 21

Glu Asn Leu Tyr Phe Gln Gly
 1               5

<210> SEQ ID NO 22
<211> LENGTH: 16
<212> TYPE: PRT
<213> ORGANISM: Artificial Sequence
<220> FEATURE:
<223> OTHER INFORMATION: biomolecule transduction peptide

<400> SEQUENCE: 22

Met Gly Cys Val Cys Ser Ser Asn Pro Glu Asp Asp Trp Met Glu Asn
 1               5                  10                  15
```